US006992103B2

(12) United States Patent
Faller et al.

(10) Patent No.: US 6,992,103 B2
(45) Date of Patent: Jan. 31, 2006

(54) BENZAMIDE DERIVATIVES, PROCESSES FOR THEIR PREPARATION, AND THEIR PHARMACEUTICAL USE

(75) Inventors: Andrew Faller, Windlesham (GB); David Timothy MacPherson, Harlow (GB); Peter Henry Milner, Harlow (GB); Steven James Stanway, Harlow (GB); Leontine Saskia Trouw, Stevenage (GB)

(73) Assignee: SmithKline Beecham P.L.C., Brentford (GB)

( * ) Notice: Subject to any disclaimer, the term of this patent is extended or adjusted under 35 U.S.C. 154(b) by 0 days.

(21) Appl. No.: 10/496,269

(22) PCT Filed: Nov. 29, 2002

(86) PCT No.: PCT/EP02/13515

§ 371 (c)(1),
(2), (4) Date: Oct. 29, 2004

(87) PCT Pub. No.: WO03/045913

PCT Pub. Date: Jun. 5, 2003

(65) Prior Publication Data

US 2005/0085520 A1    Apr. 21, 2005

(30) Foreign Application Priority Data

Nov. 30, 2001  (GB) .................................. 0128748
Jun. 18, 2002  (GB) .................................. 0214090

(51) Int. Cl.
*A61K 31/4015*  (2006.01)
*A61K 31/4166*  (2006.01)
*A61K 31/4439*  (2006.01)
*C07D 207/24*   (2006.01)
*C07D 223/10*   (2006.01)

(52) U.S. Cl. .................. 514/424; 514/376; 514/343; 514/327; 514/212.03; 548/519; 548/229; 548/550; 540/531; 546/243

(58) Field of Classification Search .......... 548/550, 548/229; 546/243; 514/424, 376
See application file for complete search history.

(56) References Cited

U.S. PATENT DOCUMENTS 5,869,024 A     2/1999  Ranganathan
2004/0171881 A1 * 9/2004  John et al. .................. 564/163

FOREIGN PATENT DOCUMENTS

EP           0 431 838           6/1991

* cited by examiner

*Primary Examiner*—Taofiq Solola
*Assistant Examiner*—Andrew B. Freistein
(74) *Attorney, Agent, or Firm*—Bonnie L. Deppenbrock

(57) ABSTRACT

The present invention relates to novel hydroxyethylene compounds having Asp2 (β-secretase, BACE1 or Memapsin) inhibitory activity, processes for their preparation, to compositions containing them and to their use in the treatment of diseases characterised by elevated β-amyloid levels or β-amyloid deposits, particularly Alzheimer's disease.

25 Claims, No Drawings

BENZAMIDE DERIVATIVES, PROCESSES FOR THEIR PREPARATION, AND THEIR PHARMACEUTICAL USE

This application is filed pursuant to 35 U.S.C. § 371 as a United States National Phase Application of International Application No. PCT/EP02/13515 filed Nov. 29, 2002, which claims priority from GB0128748.1 filed Nov. 30, 2001 and GB0214090.3 filed Jun. 18, 2002.

The present invention relates to novel hydroxyethylene compounds having Asp2 (β-secretase, BACE1 or Memapsin) inhibitory activity, processes for their preparation, to compositions containing them and to their use in the treatment of diseases characterised by elevated β-amyloid levels or β-amyloid deposits, particularly Alzheimer's disease.

Alzheimer's disease is a degenerative brain disorder in which extracellular deposition of Aβ in the form of senile plaques represents a key pathological hallmark of the disease (Selkoe, D. J. (2001) Physiological Reviews 81: 741–766). The presence of senile plaques is accompanied by a prominent inflammatory response and neuronal loss. Aβ exists in soluble and insoluble, fibrillar forms and a specific fibrillar form has been identified as the predominant neurotoxic species (Vassar, R. and Citron, M. (2000) Neuron 27: 419–422). In addition it has been reported that dementia correlates more closely with the levels of soluble amyloid rather than plaque burden (Naslund, J. et al. (2000) J. Am. Med. Assoc. 12: 1571–1577; Younkin, S. (2001) Nat. Med. 1: 8–19). Aβ is known to be produced through the cleavage of the beta amyloid precursor protein (also known as APP) by an aspartyl protease enzyme known as Asp2 (also known as β-secretase, BACE1 or Memapsin) (De Strooper, B. and Konig, G. (1999) Nature 402: 471–472).

Therefore, it has been proposed that inhibition of the Asp2 enzyme would reduce the level of APP processing and consequently reduce the levels of Aβ peptides found within the brain. Therefore, it is also thought that inhibition of the Asp2 enzyme would be an effective therapeutic target in the treatment of Alzheimer's disease.

APP is cleaved by a variety of proteolytic enzymes (De Strooper, B. and Konig, G. (1999) Nature 402: 471–472). The key enzymes in the amyloidogenic pathway are Asp2 (β-secretase) and γ-secretase both of which are aspartic proteinases and cleavage of APP by these enzymes generates Aβ. The non-amyloidogenic, α-secretase pathway, which precludes Aβ formation, has been shown to be catalysed by a number of proteinases, the best candidate being ADAM10, a disintegrin and metalloproteinase. Asp1 has been claimed to show both α- and β-secretase activity in vitro. The pattern of expression of Asp1 and Asp2 are quite different, Asp2 is most highly expressed in the pancreas and brain while Asp1 expression occurs in many other peripheral tissues. The Asp2 knockout mouse indicates that lack of Asp2 abolished Aβ production and also shows that in this animal model endogenous Asp1 cannot substitute for the Asp2 deficiency (Luo, Y. et al. (2001) Nat Neurosci. 4: 231–232; Cai, H. et. al. (2001) Nat Neurosci. 4: 233–234; Roberds, S. L. et al. (2001) Hum. Mol. Genet. 10: 1317–1324).

For an agent to be therapeutically useful in the treatment of Alzheimer's disease it is preferable that said agent is a potent inhibitor of the Asp2 enzyme, but should ideally also be selective for Asp2 over other enzymes of the aspartyl proteinase family, e.g Cathepsin D (Connor, G. E. (1998) Cathepsin D in Handbook of Proteolytic Enzymes, Barrett, A. J., Rawlings, N. D., & Woesner, J. F. (Eds) Academic Press London. pp 828–836).

WO 01/70672 (Elan Pharmaceuticals Inc.) describe a series of hydroxyethylene compounds having β-secretase activity which are implicated to be useful in the treatment of Alzheimer's disease.

We have found a novel series of compounds which are potent inhibitors of the Asp2 enzyme, thereby indicating the potential for these compounds to be effective in the treatment of Alzheimer's disease.

Thus, according to a first aspect of the present invention we provide a compound of formula (I):

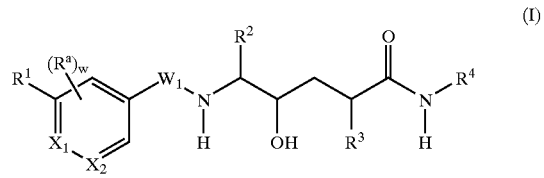

wherein
$R_1$ represents a group of formula $Z^a$ or $Z^b$:

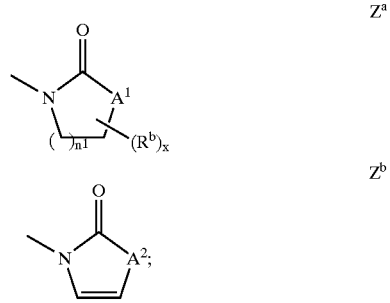

$A^1$ represents $CH_2$, O, S or $NR^5$;
$A^2$ represents O, S or $NR^5$;
$n^1$ represents an integer from 1 to 3;
$R^5$ represents hydrogen, $C_{1-6}$ alkyl optionally substituted by one or more $R^{11}$ groups, $C_{3-8}$ cycloalkyl optionally substituted by one or more $R^{11}$ groups, —$C_{1-2}$ alkyl-$C_{3-8}$ cycloalkyl or aryl;
$R^a$ represents halogen;
$R^b$ represents —$C_{1-6}$ alkyl optionally substituted by one or more $R^{11}$ groups, or —$C_{1-6}$ alkyl-aryl;
$X_1$ represents N, —C(—$R^6$)— or —C(—O—$R^7$)—;
$X_2$ represents N, —C(—$R^8$)— or —C(—Y—$R^9$)—;
Y represents a bond, $CH_2$, O, S, CO, $NR^{10}$, —N($R^{10}$)C(O)—, —C(O)N($R^{10}$)—, COO, aryl, heterocyclyl or heteroaryl;
$R^6$ represents hydrogen, halogen, —$C_{1-6}$ alkyl optionally substituted by one or more $R^{11}$ groups, —$C_{2-6}$ alkenyl, —$C_{3-8}$ cycloalkyl optionally substituted by one or more $R^{11}$ groups, —$C_{1-2}$ alkyl-$C_{3-8}$ cycloalkyl, heteroaryl, heterocyclyl or aryl;
$R^8$ represents halogen or trifluoromethyl;
$R^7$, $R^9$ and $R^{10}$ independently represent hydrogen, —$C_{1-6}$ alkyl optionally substituted by one or more $R^{11}$ groups, —$C_{2-6}$ alkenyl, —$C_{3-8}$ cycloalkyl optionally substituted by one or more $R^{11}$ groups, —$C_{1-2}$ alkyl-$C_{3-8}$ cycloalkyl, heteroaryl, heterocyclyl or aryl;
$W_1$ represents CO or $SO_2$;
$R^2$ represents —$C_{5-8}$ alkyl, —$C_{1-6}$ alkyl-aryl, —$C_{1-6}$ alkyl-heteroaryl, —$C_{1-6}$ alkyl-heterocyclyl, —$C_{1-6}$ alkyl-$C_{3-8}$ cycloalkyl, —$C_{1-6}$ alkyl-S-aryl, —$C_{1-6}$ alkyl-O-aryl, —$C_{1-6}$ alkyl-S-heteroaryl or —$C_{1-6}$ alkyl-O-heteroaryl;

$R^3$ represents —$C_{1-6}$ alkyl optionally substituted by one or more $R^{11}$ groups, or propargyl;

$R^4$ represents —$C_{1-6}$ alkyl optionally substituted by one or more $R^{11}$ groups, —$C_{1-6}$ alkyl-aryl, —$C_{1-6}$ alkyl-heteroaryl, —$C_{1-6}$ alkyl-heterocyclyl, —$C_{1-6}$ alkyl-$C_{3-8}$ cycloalkyl, —$C_{3-8}$ cycloalkyl optionally substituted by one or more groups selected from $R^{11}$ and $C_{1-6}$ alkyl, or propargyl;

w and x independently represent an integer from 0 to 2;

$R^{11}$ represents halogen, hydroxy, —COOH, —COOCH$_3$, $C_{1-6}$ alkoxy, cyano or amino;

or a pharmaceutically acceptable salt or solvate thereof.

References to alkyl include references to both straight chain and branched chain aliphatic isomers of the corresponding alkyl. It will be appreciated that references to alkenyl shall be interpreted similarly.

References to $C_{3-8}$ cycloalkyl include references to all alicyclic (including bridged) isomers of the corresponding alkyl.

References to 'aryl' include references to monocyclic carbocyclic aromatic rings (eg. phenyl) and bicyclic carbocyclic aromatic rings (e.g. naphthyl).

References to 'heteroaryl' include references to mono- and bicyclic heterocyclic aromatic rings containing 1–4 hetero atoms selected from nitrogen, oxygen and sulphur. Examples of monocyclic heterocyclic aromatic rings include e.g. thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl, pyridyl, tetrazolyl and the like. Examples of bicyclic heterocyclic aromatic rings include eg. quinolinyl, isoquinolinyl, quinazolinyl, quinoxalinyl, cinnolinyl, naphthyridinyl, indolyl, indazolyl, pyrrolopyridinyl, benzofuranyl, benzothienyl, benzimidazolyl, benzoxazolyl, benzisoxazolyl, benzothiazolyl, benzisothiazolyl, benzoxadiazolyl, benzothiadiazolyl and the like.

References to 'heterocyclyl' include references to a 5–7 membered non-aromatic monocyclic ring containing 1 to 3 heteroatoms selected from nitrogen, sulphur or oxygen. Examples of heterocyclic non-aromatic rings include morpholinyl, piperidinyl, piperazinyl, thiomorpholinyl, oxathianyl, dithianyl, dioxanyl, pyrrolidinyl, dioxolanyl, oxathiolanyl, imidazolidinyl, pyrazolidinyl and the like.

Carbocyclic and heterocyclic aromatic and non-aromatic heterocyclic rings may be optionally substituted, e.g. by one or more $C_{1-6}$ alkyl, $C_{2-6}$ alkenyl, halogen, $C_{1-6}$ alkoxy, CN, hydroxy, =O, nitro, —NHCOC$_{1-6}$ alkyl, —OCF$_3$, —CF$_3$, —COOH, —COOC$_{1-6}$ alkyl, —OCHF$_2$, —SCF$_3$, —NR$^{12}$R$^{13}$, — CONR$^{12}$R$^{13}$, —SO$_2$NR$^{12}$R$^{13}$ (wherein R$^{12}$ and R$^{13}$ independently represent hydrogen, $C_{1-6}$ alkyl or $C_{3-8}$ cycloalkyl), —NHSO$_2$CH$_3$, —SO$_2$CH$_3$ or —SCH$_3$ groups.

Alkyl moieties are more preferably $C_{1-4}$ alkyl.

Preferably, $R^1$ represents $Z^a$.

Preferably, $A^1$ represents O or CH$_2$, most preferably CH$_2$.

When $A^1$ represents O, x preferably represents 1.

Preferably, $n^1$ represents 1.

Preferably, $X_1$ represents —C—(R$^6$) or N, most preferably —C—(R$^6$).

Preferably, $R^6$ represents hydrogen or halogen, most preferably hydrogen.

Preferably, $X_2$ represents —C—(Y—R$^9$)— or —C(—R$^8$)—, most preferably —C—(Y—R$^9$)—.

When $X_2$ represents —C(—R$^8$)—, R$^8$ is preferably trifluoromethyl.

When $X_2$ represents —C—(Y—R$^9$)—, preferably:

Y represents O and R$^9$ represents hydrogen, $C_{1-6}$ alkyl (particularly n-propyl, methyl, CH(CH$_3$)$_2$ or —CH(CH$_3$)(C$_2$H$_5$)), or $C_{1-6}$ alkyl substituted with a hydroxy, $C_{1-6}$ alkoxy or $C_{3-8}$ cycloalkyl group (particularly —(CH$_2$)$_2$—OH, —(CH$_2$)$_3$—O—CH$_3$ or —CH$_2$-cyclopropyl), aryl (particularly phenyl), $C_{2-6}$ alkenyl (particularly propenyl), $C_{3-8}$ cycloalkyl, (particularly cyclobutyl) or a $C_{1-6}$ alkoxy group (particularly methoxy); or Y represents a bond and R$^9$ represents hydrogen, heterocyclyl (particularly 2-oxopyrrolidin-1-yl), aryl (particularly phenyl); or Y represents —N(R$^{10}$)C(O)— (particularly NHCO) and R$^9$ represents $C_{1-6}$ alkyl (particularly methyl); or Y represents —C(O)N(R$^{10}$)— (particularly CONMe) and R$^9$ represents $C_{1-6}$ alkyl (particularly propyl).

Most preferably, Y represents a bond, O or —N(H)C(O)—.

Most preferably, R$^9$ represents hydrogen, $C_{1-6}$ alkyl (particularly methyl or CH(CH$_3$)$_2$) or heterocyclyl (particularly 2-oxopyrrolidin-1-yl).

When Y represents bond, R$^9$ is most preferably hydrogen or 2-oxopyrrolidin-1-yl.

When Y represents O, R$^9$ is most preferably CH(CH$_3$)$_2$.

When Y represents NHCO, R$^9$ is most preferably methyl.

Preferably, $W_1$ represents CO.

Preferably, $R^2$ represents benzyl optionally substituted with one or more halogen atoms (eg. fluorine). Most preferably, $R^2$ represents unsubstituted benzyl.

Preferably, $R^3$ represents methyl, 3-methyl butyl or propargyl, most preferably methyl.

Preferably, $R^4$ represents —$C_{1-6}$ alkyl (particularly 3,3-dimethyl butyl or —CH$_2$—CH(CH$_3$)$_2$), —$C_{3-8}$ cycloalkyl (particularly norbornyl, cyclobutyl or cyclohexyl) optionally substituted by one or two $C_{1-6}$ alkyl groups (particularly methyl or t-butyl), —$C_{1-6}$ alkyl-$C_{3-8}$ cycloalkyl (particularly —CH$_2$-cyclopropyl or —(CH$_2$)$_2$-cyclohexyl), or propargyl.

Most preferably, $R^4$ represents —$C_{3-8}$ cycloalkyl (particularly norbornyl, cyclobutyl or cyclohexyl) optionally substituted by one or two —$C_{1-6}$ alkyl groups (particularly dimethylcyclohexyl or t-butylcyclohexyl).

Preferably, w represents 0 or 1.

Preferably, x represents 0 or 1. More preferably, x represents 0.

When present, R$^a$ preferably represents fluorine.

When present, R$^b$ preferably represents —$C_{1-6}$ alkyl (particularly CH(CH$_3$)$_2$) or —$C_{1-6}$ alkyl-aryl (particularly benzyl).

Preferred compounds according to the invention include examples E1–E35 as shown below, or a pharmaceutically acceptable salt thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1–19, such as acid addition salts formed with inorganic or organic acids e.g. hydrochlorides, hydrobromides, sulphates, phosphates, acetates, benzoates, citrates, nitrates, succinates, lactates, tartrates, fumarates, maleates, 1-hydroxy-2-naphthoates, palmoates, methanesulphonates, p-toluenesulphonates, naphthalenesulphonates, formates or trifluoroacetates. The present invention includes within its scope all possible stoichiometric and non-stoichiometric forms.

The compounds of formula (I) may be prepared in crystalline or non-crystalline form, and, if crystalline, may optionally be solvated, eg. as the hydrate. This invention includes within its scope stoichiometric solvates (eg. hydrates) as well as compounds containing variable amounts of solvent (eg. water).

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof. Preferably, compounds of formula (I) are in the form of a single enantiomer of formula (Ia):

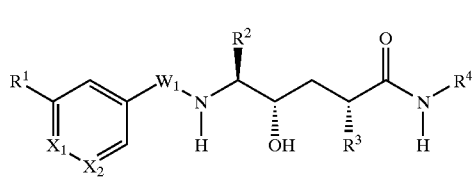

(Ia)

The compounds of formula (I) and salts and solvates thereof may be prepared by the methodology described hereinafter, constituting a further aspect of this invention.

A process according to the invention for preparing a compound of formula (I) which comprises:
(a) reacting a compound of formula (II)

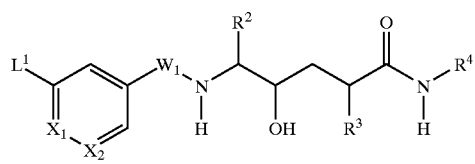

(II)

optionally with any hydroxy or amino groups protected, wherein $X_1$, $X_2$, $R^2$, $R^3$, $R^4$ and $W_1$ are defined above and $L^1$ represents a suitable leaving group, eg. a halogen atom, such as bromine atom, with a compound of formula $R^1$—H, wherein $R^1$ is as defined above, and thereafter optionally as necessary deprotecting a compound of formula (I) which is protected; or
(b) reacting a compound of formula (III)

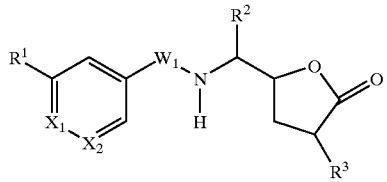

(III)

optionally with any hydroxy or amino groups protected, wherein $R^1$, $X_1$, $X_2$, $R^2$, $R^3$ and $W_1$ are as defined above, with a compound of formula
$R^4$—$NH_2$, wherein $R^4$ is as defined above, and thereafter optionally as necessary deprotecting a compound of formula (I) which is protected; or (c) preparing a compound of formula (I) wherein $W_1$ represents CO which comprises reacting a compound of formula (IV)

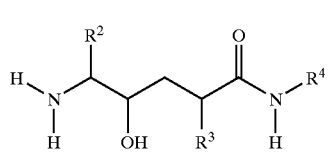

(IV)

optionally with any hydroxy or amino groups protected, wherein $R^2$, $R^3$ and $R^4$ are as defined above, with a compound of formula (Va)

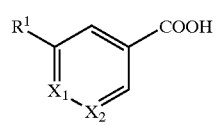

(Va)

or an activated and optionally protected derivative thereof, wherein $R^1$, $X_1$ and $X_2$ are as defined above, and thereafter optionally as necessary deprotecting a compound of formula (I) which is protected; or
(d) preparing a compound of formula (I) wherein $W_1$ represents $SO_2$ which comprises reacting a compound of formula (IV)

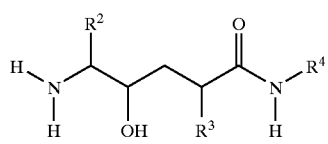

(IV)

optionally with any hydroxy or amino groups protected, wherein $R^2$, $R^3$ and $R^4$ are as defined above, with a compound of formula (Vb)

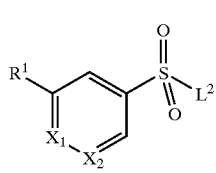

(Vb)

or an optionally protected derivative thereof, wherein $R^1$, $X_1$ and $X_2$ are as defined above and $L^2$ represents a suitable leaving group, such as a halogen atom (eg. chlorine), and thereafter optionally as necessary deprotecting a compound of formula (I) which is protected; or
(e) deprotecting a compound of formula (I) which is protected; or
(f) interconversion of compounds of formula (1) to other compounds of formula (I).

Process (a) typically comprises heating a compound of formula (II) and the compound of formula $R^1$—H in a suitable solvent such as 1,4-dioxane with a suitable base (such as caesium carbonate) with an appropriate catalyst (e.g. see Organic Letters (2000), 2, 1101–1104).

Process (b) typically comprises heating a mixture of compounds of formula (III) and $R^4$—$NH_2$.

Process (c) is a conventional amide coupling reaction where the activated derivative may be, for example, the acid chloride, mixed anhydride, active ester or O-acyl-isourea. The reaction typically comprises mixing compounds of formulae (IV) and (Va) with a suitable coupling agent (such as N-cyclohexylcarbodiimide-N'-methyl polystyrene in the presence of HOBT) in a suitable solvent (such as dimethylformamide or dichloromethane) at a suitable temperature e.g. room temperature.

Process (d) typically comprises the use of a suitable base, eg. N-methylmorpholine or polystyrene-N-methylmorpholine in the presence of catalytic (10%) dimethylaminopyridine (DMAP) in a suitable solvent eg. dimethylformamide and/or dichloromethane.

In process (e), examples of protecting groups and the means for their removal can be found in T. W. Greene and P. G. M. Wuts 'Protective Groups in Organic Synthesis' (J. Wiley and Sons, 3rd Ed. 1999). Suitable amine protecting groups include sulphonyl (e.g. tosyl), acyl (e.g. benzyloxycarbonyl or t-butoxycarbonyl) and arylalkyl (e.g. benzyl), which may be removed by hydrolysis or hydrogenolysis as appropriate. Other suitable amine protecting groups include trifluoroacetyl (—COCF$_3$) which may be removed by base catalysed hydrolysis. Suitable hydroxy protecting groups would be silyl based groups such as t-butyldimethylsilyl, which may be removed using standard methods, for example use of an acid such as trifluoroacetic or hydrochloric acid or a fluoride source such as tetra n-butylammonium fluoride.

Process (f) may be performed using conventional interconversion procedures such as epimerisation, oxidation, reduction, alkylation, nucleophilic aromatic substitution, ester hydrolysis, amide bond formation, t-butoxycarbonyl group addition or removal and sulphonylation.

Compounds of formula (IV) and compounds of formula (II) wherein $W_1$ represents CO may be prepared in accordance with the following procedure:

wherein $R^2$, $R^3$, $R^4$, $X_1$ and $X_2$ are as defined above, $P^1$ represents a suitable protecting group such as t-butoxycarbonyl and $L^1$ represents a suitable leaving group, eg. a halogen atom, such as bromine atom.

Step (i) typically comprises heating a compound of formula (VI) in neat amine $R^4$—$NH_2$ to a suitable temperature e.g. 60° C.

Step (ii) typically comprises the use of mixing a compound of formula (VII) with a suitable acid (such as trifluoroacetic acid) in a suitable solvent (such as dichloromethane) at a suitable temperature e.g. room temperature.

Step (iii) typically comprises the use of mixing compounds of formulae (IV) and (VIII) with a suitable coupling agent (such as N-cyclohexylcarbodiimide-N'-methyl polystyrene in the presence of HOBT) in a suitable solvent (such as dichloromethane or dimethylformamide) at a suitable temperature e.g. room temperature.

Compounds of formula (III) wherein $W_1$ represents CO may be prepared in accordance with the following procedure:

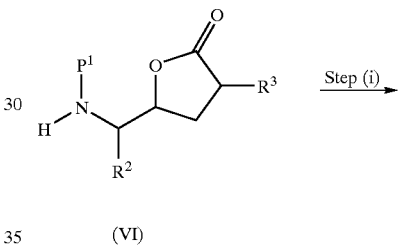

(VI)

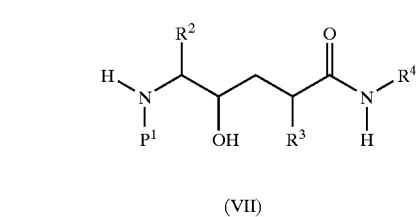

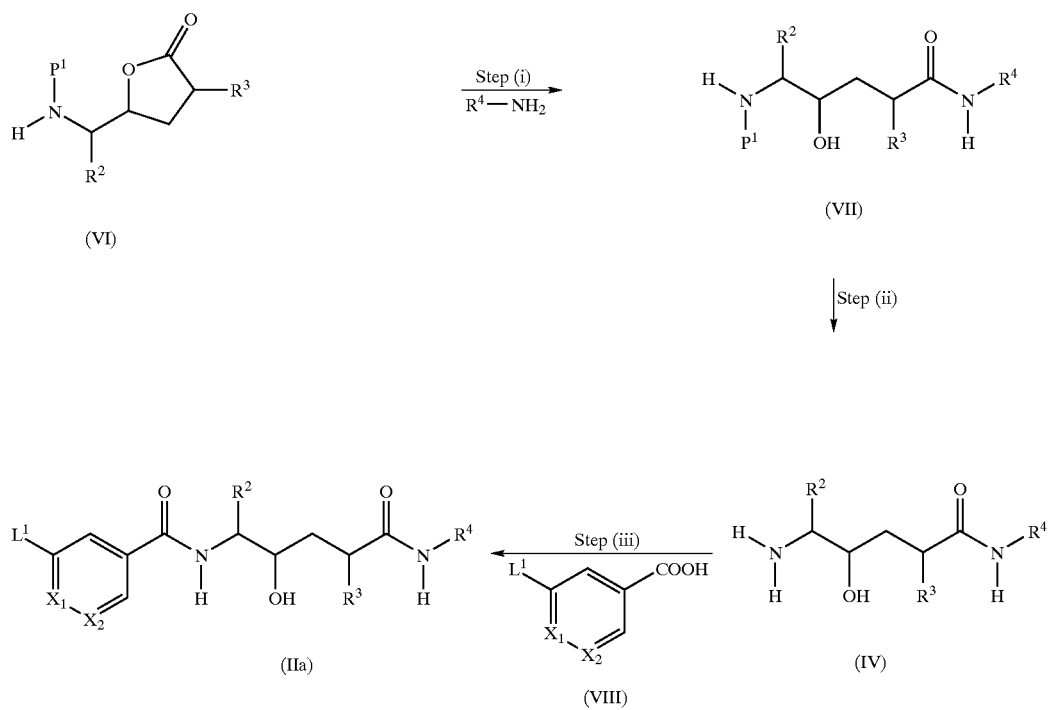

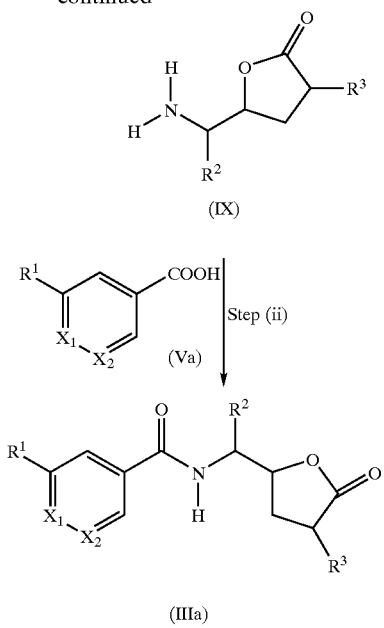

$R^1$, $X_1$, $X_2$, $R^2$ and $R^3$ are as defined above and $P^1$ represents a suitable protecting group such as t-butoxycarbonyl.

Step (i) typically comprises mixing a compound of formula (VI) with a suitable acid (such as trifluoroacetic acid) in a suitable solvent (such as dichloromethane) at a suitable temperature e.g. room temperature.

Step (ii) typically comprises mixing compounds of formulae (IX) and (Va) with a suitable coupling agent (such as N-cyclohexylcarbodiimide-N'-methyl polystyrene) in a suitable solvent (such as dimethylformamide or dichloromethane) at a suitable temperature e.g. room temperature.

Compounds of formula (III) where $W_1$ represents $SO_2$ may be prepared in an identical manner to the process described above for preparing compounds of formula (H) where $W_1$ represents CO, with the exception that in step (ii), a compound of formula (Vb) as defined above is used in place of a compound of formula (Va) and that the conditions of process (d) described above are used in place of those described for step (ii).

Compounds of formula (VI) may be prepared in accordance with the synthesis described in Journal of Organic Chemistry (1986) 51(21), 3921.

Compounds of formula (Va), (Vb) and (VIII) are either known and/or may be obtained commercially and/or may be prepared in accordance with known procedures.

As a further aspect of the invention there is thus provided a compound of formula (I) or a pharmaceutically acceptable salt or solvate thereof for use as a pharmaceutical, particularly in the treatment of patients with diseases characterised by elevated β-amyloid levels or β-amyloid deposits.

According to another aspect of the invention, there is provided the use of a compound of formula (I) or a physiologically acceptable salt or solvate thereof for the manufacture of a medicament for the treatment of patients with diseases characterised by elevated β-amyloid levels or β-amyloid deposits.

In a further or alternative aspect there is provided a method for the treatment of a human or animal subject with diseases characterised by elevated β-amyloid levels or β-amyloid deposits, which method comprises administering to said human or animal subject an effective amount of a compound of formula (I) or a physiologically acceptable salt or solvate thereof.

As a further aspect of the invention there is thus provided a pharmaceutical composition comprising a compound of formula (I) or a pharmaceutically acceptable salt or solvate thereof for use in the treatment of diseases characterised by elevated β-amyloid levels or β-amyloid deposits.

It will be appreciated by those skilled in the art that reference herein to treatment extends to prophylaxis as well as the treatment of diseases characterised by elevated β-amyloid levels or β-amyloid deposits.

The compounds according to the invention may be formulated for administration in any convenient way, and the invention therefore also includes within its scope pharmaceutical compositions for use in the therapy of diseases characterised by elevated β-amyloid levels or β-amyloid deposits, comprising a compound of formula (I) or a physiologically acceptable salt or solvate thereof together, if desirable, with one or more physiologically acceptable diluents or carriers.

It will be appreciated that diseases characterised by elevated β-amyloid levels or β-amyloid deposits include Alzheimer's disease, mild cognitive impairment, Down's syndrome, hereditary cerebral haemorrhage with β-amyloidosis of the Dutch type, cerebral β-amyloid angiopathy and various types of degenerative dementias, such as those associated with Parkinson's disease, progressive supranuclear palsy, cortical basal degeneration and diffuse Lewis body type of Alzheimer's disease.

Most preferably, the disease characterised by elevated β-amyloid levels or β-amyloid deposits is Alzheimer's disease.

There is also provided a process for preparing such a pharmaceutical formulation which comprises mixing the ingredients.

The compounds according to the invention may, for example, be formulated for oral, inhaled, intranasal, buccal, enteral, parenteral, topical, sublingual, intrathecal or rectal administration, preferably for oral administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

When the compounds of the invention are administered topically they may be presented as a cream, ointment or patch.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20 mg, for example 0.2 to 5 mg; and such unit doses may be administered more than once a day, for example one, two, three or four times per day (preferably once or twice), so that the total daily dosage is in the range of about 0.5 to 100 mg; and such therapy may extend for a number of weeks or months.

All publications, including but not limited to patents and patent applications, cited in this specification are herein incorporated by reference as if each individual publication were specifically and individually indicated to be incorporated by reference herein as though fully set forth.

EXAMPLES

Description 1

[(1S,2S,4R)-1-Benzyl-4-(3,3-dimethylbutylcarbamoyl-2-hydroxypentyl]-carbamic acid t-butyl ester (D1)

[(S)-1-(4-Methyl-5-oxo-tetrahydrofuran-2-yl)-2-phenyl-ethyl]arbamic acid t-butyl ester (synthesis described in Journal of Organic Chemistry (1986) 51(21), 3921) (245 mg, 0.77 mmol) was treated with 3,3-dimethyl butylamine (1.0 g, 9.9 mmol) and the resulting solution was heated at 70° C. for 24 h. The solution was then evaporated to dryness and the residue was partitioned between 1M hydrochloric acid and ethyl acetate. The organic phase was separated and washed with further 1M hydrochloric acid and brine. It was then dried over MgSO$_4$, filtered and evaporated to afford the crude product as a white foam (303 mg). Purification by chromatography on silica eluting with 0–2% methanol in dichloromethane gave the title compound (D1) (264 mg, 82%).

MS (ES) MNa$^+$=443

$^1$H NMR (400 MHz, CDCl$_3$) 0.92 (9H, s), 1.10 (3H, d, J 7.2 Hz), 1.30–1.43 (11H, m), 1.57–1.75 (2H, m), 2.50 (1H, m), 2.90 (2H, m), 3.24 (2H, m), 3.66 (2H, m), 3.80 (1H, d, J 4.4 Hz), 4.85 (1H, br.d), 5.68 (1H, br.s) and 7.15–7.30 (5H, m).

Description 2

(2R,4S,5S)-5-Amino-4-hydroxy-2-methyl-6-phenyl-hexanoic acid (3,3-dimethylbutyl)-amide (D2)

[(1S,2S,4R)-1-Benzyl-4-(3,3-dimethylbutylcarbamoyl)-2-hydroxypentyl]-carbamic acid t-butyl ester (D1) (264 mg, 0.63 mmol) was treated with 4M HCl in dioxane (5 ml) and the resulting solution was stirred at room temperature for 1 h. It was then evaporated to dryness and the residue was partitioned between satd. aq. sodium carbonate and ethyl acetate. The aqueous layer was separated and extracted with further ethyl acetate. The combined organic extracts were washed with brine, dried over MgSO$_4$, filtered and evaporated to afford product (179 mg, 89%).

MS (ES) MH$^+$=321

$^1$H NMR (400 MHz, CDCl$_3$) 0.93 (9H, s), 1.18 (3H, d, J 7.0 Hz), 1.40 (2H, t, J 8.5 Hz), 1.48 (1H, m), 1.60–1.90 (3H, br.s), 1.88 (1H, m), 2.48 (1H, dd, J 9.5, 14.0 Hz), 2.59 (1H, m), 2.82 (1H, m), 2.94 (1H, dd, J 4.0, 14.0 Hz), 3.20–3.37 (3H, m), 5.81 (1H, br.s.) and 7.13–7.33 (5H, m).

Description 3

N-[(1S,2S,4R)-1-Benzyl-4-(3,3-dimethylbutylcar-bamoyl)-2-hydroxypentyl]-3-bromo-4-fluorobenza-mide (D3)

N-Cyclohexylcarbodiimide-N'-methyl polystyrene (265 mg @ 1.70 mmol/g; ex. Novabiochem) was treated with a solution of 1-hydroxybenzotriazole (0.45 mmol) in DMF (1.0 ml) followed by 3-bromo-4-fluorobenzoic acid (99 mg, 0.45 mmol), dichloromethane (1 ml) and (2R,4S,5S)-5-amino-4-hydroxy-2-methyl-6-phenylhexanoic acid (3,3-dimethylbutyl)-amide (D2) (90 mg, 0.30 mmol) in dichloromethane (0.5 ml)/DMF (0.5 ml). After stirring gently overnight at room temperature, methylisocyanate polystyrene (150 mg @ 1.80 mmol/g; ex. Novabiochem) and tris-(2-aminoethyl)-amine polystyrene (250 mg @ 3.20 mmol/g; ex. Novabiochem) were added and the mixture was stirred for a further 1.5 h. It was then filtered and the spent resins were washed with DMF and dichloromethane. The combined filtrates were evaporated to dryness and the residue was filtered through a short column of silica gel to give the title compound, 126 mg.

MS (ES) MH$^+$=521, 523

Description 4

3-Bromo-5-nitro-benzoic acid (D4)

To a mixture of 3-amino-5-nitro-benzoic acid (8.0 g) in 48% aqueous HBr (90 ml) at 0° C. was added sodium nitrite (4.0 g) over 15 minutes. The resulting solution of diazonium salt was added to CuBr (4.0 g) in 48% HBr (10 ml) at 60–70° C. at such a rate to maintain the temperature at 60–70° C. After completion of the addition, the mixture was warmed to 70° C. for 45 minutes. The mixture was cooled to room temperature, water (500 ml) was added and the product was extracted into ether (3×). The combined extracts were washed with water (2×), dried over sodium sulfate and evaporated to give a beige solid, 10.53 g.

MS (APCI) M−H=244, 246

Description 5

3-Nitro-5-(2-oxopyrrolidin-1-yl)-benzoic acid (D5)

The title compound was prepared as for E1 from 3-bromo-5-nitro-benzoic acid (D4)

$^1$H NMR (DMSO-d$_6$) 2.11 (2H, m), 2.55 (4H, m), 8.36 (1H, s), 8.52 (1H, s), 8.82 (1H, s).

Description 6

3-Hydroxy-5-(2-oxopyrrolidin-1-yl)-benzoic acid (D6)

A mixture of 3-nitro-5-(2-oxopyrrolidin-1-yl)-benzoic acid (D5) (2.86 g) and 10% Pd—C (0.7 g) in methanol (450 ml) water (50 ml) was hydrogenated at atmospheric pressure for 3 hrs. The mixture was filtered through Celite and concentrated to give 3-amino-5-(2-oxopyrrolidin-1-yl)-benzoic acid (2.70 g).

This amine (1.10 g, 5.0 mmol) in 2N HCl (10 ml) and methanol (approx 15 ml, to aid solubility) was cooled in an ice bath and treated portionwise with sodium nitrite (0.76 g, 11.0 mmol) at such a rate to keep the temperature below 5° C. After completion of the addition, water (20 ml) was added and the mixture was heated at approx 90° C. for 1 hr. After cooling the product was extracted into ethyl acetate and the combined extracts were washed with brine and then dried over sodium sulfate and evaporated to give the title compound, 0.93 g.

MS (ES) M−H=220

$^1$H NMR (DMSO-d$_6$) 2.03 (2H, m), 2.50 (2H, m, partially obscured by solvent), 3.81 (2H, m), 7.11 (1H, s with fine splitting), 7.44 (1H, s with fine splitting), 7.61 (1H, s with fine splitting), 9.84 (1H, s), 12.90 (1H, broad s)

Description 7

3,5-Bis-(2-oxo-pyrrolidin-1-yl)benzoic acid methyl ester (D7)

To a solution of 3-bromo-5-iodobenzoic acid methyl ester (588 mg, 1.72 mmol) in dioxane (10 ml) was added 2-pyrrolidinone (120 µl, 1.14 mmol), Cs$_2$CO$_3$ (720 mg, 2.21 mmol), xantphos (51 mg, 0.09 mmol) and pd$_2$(dba)$_3$ (28 mg, 0.03 mmol). The reaction mixture was stirred at 100° C. overnight, then cooled down to room temperature and filtered through celite and concentrated in vacuo. The product was purified by column chromatography (EtOAc) which yielded D7 (411 mg) as light yellow solid.

MS (ES) M+H=303; $^1$H NMR (400 MHz, CDCl$_3$) 2.14–2.22 (4H, m), 2.61–2.66 (4H, m), 3.92 (3H, s), 3.91–3.95 (4H, m), 7.97 (2H, d, J=2 Hz), 8.45–8.46 (1H, t, J=2 Hz).

Description 8

3,5-Bis-(2-oxopyrrolidin-1-yl)benzoic acid (D8)

A solution of 3,5-bis-(2-oxopyrrolidin-1-yl)benzoic acid methyl ester (D7) (201 mg, 0.666 mmol) in dioxane (2 ml) was treated with LiOH (42 mg, 0.998 mmol) and water (1 ml). The reaction mixture was stirred for 2 hours at room temperature. The solvent was then evaporated to dryness and the residue was partitioned between ethyl acetate and water. The aqueous layer was separated and acidified to pH=1. The product precipitated in the aqueous layer and was removed by filtration and dried in vacuo to D8 (128 mg) as white solid.

MS (ES) M+H=289.

Description 9

3-Bromo-5-(2-oxopyrrolidin-1-yl)benzoic acid methyl ester (D9)

3-Bromo-5-iodobenzoic acid methyl ester (2.044 g, 5.996 mmol) in dioxane (25 ml) was treated with 2-pyrrolidinone (433 µl, 5.696 mmol), Cs$_2$CO$_3$ (2.93 g, 8.994 mmol), pd$_2$(dba)$_3$ (110 mg, 0.12 mmol) and Xantphos (208 mg, 0.36 mmol). The reaction mixture was heated to 40° C. for 3 days, then cooled to room temperature. The reaction mixture was filtered through celite and concentrated in vacuo. Column chromatography on silica gel (EtOAc) gave D9 (1.4 g) as a brown solid.

MS (ES) M+H=299.

Description 10

5-(2-Oxopyrrolidin-1-yl)-biphenyl-3-carboxylic acid methyl ester (D10)

To 3-bromo-5-(2-oxopyrrolidin-1-yl)benzoic acid methyl ester (D9) (70 mg, 0.235 mmol) in DME (2 ml) was added Na$_2$CO$_3$ (290 µl, 2M, 0.588 mmol), benzeneboronic acid (29 mg, 0.235 mmol) and Pd(OAc)$_2$ (3 mg, 0.013 mmol). The mixture was stirred at 85° C. for 2 days. The reaction mixture was cooled down, filtrated through celite and evaporated in vacuo. The product was purified by column chromatography (PE:EtOAc=3:1) which yielded D10 (23 mg).

MS (ES) M+H=296.

Description 11

5-(2-Oxopyrrolidin-1-yl)-biphenyl-3-carboxylic acid (D11)

To 5-(2-oxopyrrolidin-1-yl)-biphenyl-3-carboxylic acid methyl ester (D10) (23 mg, 0.078 mmol) in dioxane (2 ml) was added LiOH (5 mg, 0.117 mmol) and water (1 ml) and stirred at room temperature for 2 hours. The solvent was then evaporated to dryness and the residue was partitioned between ethyl acetate and water. The aqueous layer was separated and acidified to pH=1. The product precipitated in the aqueous layer and was removed by filtration and dried in vacuo to afford D11 (10 mg) as white solid.

MS (ES) M+H=282, MH$^-$=280.

Description 12

Methyl 3-acetylamino-5-(2-oxopyrrolidin-1-yl)benzoate (D12)

D12 was prepared as for E1, from methyl 3-bromo-5-(2-oxopyrrolidin-1-yl)benzoate and acetamide.

$^1$H NMR (CDCl$_3$) 2.18 (5H, m), 2.63 (2H, t), 3.90 (5H, m), 7.67 (1H, br s), 7.80 (1H, m), 8.01 (1H, s), 8.27 (1H, m).

Description 13

3-Acetylamino-5-(2-oxopyrrolidin-1-yl)benzoic acid (D13)

The title compound was prepared in an analogous manner to D11, from methyl 2-acetylamino-5-(2-oxopyrrolidin-1-yl)benzoate (D12).

MS (ES) M+H=263.

Description 14

3-(3-Methoxypropoxy)-5-(2-oxopyrrolidin-1-yl) benzoic acid (D14)

A solution of the methyl ester of 3-hydroxy-5-(2-oxopyrrolidin-1-yl)-benzoic acid (D6) (300 mg, 1.28 mmol), 3-benzyloxypropan-1-ol (0.284 ml, 1.79 mmol) and triphenyl phosphine (470 mg, 1.79 mmol) in THF at room temperature was treated dropwise with DEAD (0.282 ml, 1.79 mmol). The mixture was stirred overnight at room temperature, concentrated and then chromatographed on silica gel to remove some of the impurities.

This product in methanol (15 ml) was hydrogenolysed initially with 10% Pd—C (0.25 g) at atmospheric pressure for 24 hrs and then a further 0.25 g of catalyst was added and the mixture hydrogenolysed at 50 psi for a further 48 hrs. The mixture was filtered through Celite and concentrated. Chromatography on silica gel (ethyl acetate/hexane) gave 260 mg of alcohol product. (M+H=294). This alcohol (127 mg, 0.433 mmol) in dichloromethane (2 ml) was treated with proton sponge (279 mg, 1.30 mmol) and trimethyloxonium tetrafluoroborate (192 mg, 1.30 mmol). After 3 hrs, further quantities of proton sponge (93 mg) and trimethyloxonium tetrafluoroborate (65 mg) were added and stirring was continued for a further 2 hrs. Ethyl acetate and 2N HCl were added and the product was extracted into ethyl acetate. The extracts were washed with sodium bicarbonate solution, 2N HCl and brine and then dried (Na$_2$SO$_4$) and evaporated. Chromatography on silica gel (ethyl acetate/hexane) gave 76 mg of methyl ether (M+H=308). This product in 1,4-dioxan (1.5 ml) was stirred with LiOH solution (1M, 1.5 ml) for 1 hr. Amberlyst-15 acidic ion-exchange resin was added to take the pH to ~3 and the mixture was filtered and concentrated to give a solid which was triturated with diethyl ether to give D14 (53 mg).

MS (ES+), M+H=294

Description 15

3-(2-Hydroxyethoxy)-5-(2-oxopyrrolidin-1-yl)benzoic acid (D15)

Prepared from the methyl ester of 3-hydroxy-5-(2-oxopyrrolidin-1-yl)benzoic acid (D6) by Mitsunobu reaction with 2-benzyloxyethanol, followed by saponification of the methyl ester and hydrogenolytic removal of the benzyl group.

MS (ES), M+H=266, M−H=264

Description 16

3-Isopropoxy-5-(2-oxopyrrolidin-1-yl)benzoic acid (D16)

A mixture of the methyl ester of 3-hydroxy-5-(2-oxopyrrolidin-1-yl)benzoic acid (D6) (0.705 g, 3 mmol) and caesium carbonate (1.17 g, 3.6 mmol) in DMF (10 ml) was sonicated for 5 mins. i-Propyl iodide (0.6 ml) was added and the mixture was sonicated for 4 hrs and then allowed to stand at room temperature overnight. Work up as for D14 and chromatography (ethyl acetate/hexane) gave the isopropoxy analogue (630 mg).

This product was saponified with lithium hydroxide to give D16 as a white solid (598 mg).

MS (ES), M−H=262, M+H=264

Description 17

N-[(1S,2S,4R)-1-Benzyl-4-(3,3-dimethylbutylcarbamoyl)-2-hydroxypentyl]-3-bromo-5-methoxybenzamide (D17)

Prepared as for D3 from (2R,4S,5S)-5-amino-4-hydroxy-2-methyl-6-phenylhexanoic acid (bicyclo[2.2.1]hept-2-yl) amide (D29) and 3-bromo-5-methoxybenzoic acid.

MS (ES) M−H=543, M+H=541

Description 18

3-(2-Oxooxazolidin-3-yl)benzoic acid methyl ester (D18)

Methyl 3-bromobenzoate (500 mg, 2.33 mmol), caesium carbonate (1.06 g, 3.26 mmol), oxazolidin-2-one (243 mg, 2.80 mmol), 9,9-dimethyl-4,5-bis(diphenylphosphino)xanthene (107 mg, 0.186 mmol) and tris(dibenzylideneacetone) dipalladium (0) (43 mg, 0.047 mmol) were refluxed under argon in dioxane (6 ml) for 18 h. After cooling, the mixture was filtered and evaporated in vacuo. Column chromatography on silica gel eluting with a gradient of 10–50% ethyl acetate in hexane gave the title compound (113 mg).

MS (ES) M+H=222.

Description 19

3-(2-Oxooxazolidin-3-yl)benzoic acid (D19)

3-(2-Oxooxazolidin-3-yl)benzoic acid methyl ester (D118) (110 mg, 0.5 mmol) in dioxane (2.5 ml) was treated with 1M LiOH solution (0.75 ml) and the mixture was stirred at room temperature for 1.5 h. Amberlyst 15 was then added and stirring continued for 15 mins. The resin was filtered and the filtrate evaporated to dryness. Th residue was tritutated with diethyl ether to afford the title compound (62 mg, 60%).

MS (ES) M+H=208, M−H=206.

Description 20

3-((R)+Benzyl-2-oxooxazolidin-3-yl)benzoic acid methyl ester (D20)

D20 was prepared by the method described in D18 using (R)-4-benzyl-oxazolidin-2-one in place of oxazolidin-2-one. Yield=66%.

MS (ES) M+H=312.

Description 21

3-((R)-4-Benzyl-2-oxooxazolidin-3-yl)benzoic acid (D21)

3-((R)-4-Benzyl-2-oxooxazolidin-3-yl)benzoic acid methyl ester (D20) was treated as described in D19 to afford the title acid (88%).

MS (ES) M+H=298, M−H=296.

Description 22

3-((S)-4-Isopropyl-2-oxooxazolidin-3-yl)benzoic acid methyl ester (D22)

D22 was prepared by the method described in D18 using (S)-4-isopropyl oxazolidin-2-one in place of oxazolidin-2-one. Yield=70%.
MS (ES) M+H=264.

Description 23

3-((S)-4-Isopropyl-2-oxo-oxazolidin-3-yl)benzoic acid (D23)

3-((S)-4-Isopropyl-2-oxooxazolidin-3-yl)benzoic acid methyl ester (D22) was treated as described in D19 to afford the title acid (59%).
MS (ES) M+H=264, M−H⁻=262.

Description 24

2-Fluoro-3-(2-oxopyrrolidin-1-yl)-5-trifluoromethylbenzoic acid methyl ester (D24)

3-Bromo-2-fluoro-5-trifluoromethylbenzoic acid methyl ester (500 mg, 1.95 mmol)), caesium carbonate (950 mg, 2.92 mmol), pyrrolidin-2-one (248 mg, 2.92 mmol), 9,9-dimethyl-4,5-bis(diphenylphosphino)xanthene (68 mg, 0.117 mmol) and tris(dibenzylideneacetone)dipalladium (0) (36 mg, 0.039 mmol) were refluxed under argon in dioxane (7 ml) for 18 h. After cooling, the mixture was filtered and evaporated in vacuo. Column chromatography on silica gel eluting with a gradient of 20–50% ethyl acetate in hexane gave a mixture of D24 and 3-chloro-2-(2-oxopyrrolidin-1-yl)-5-trifluoromethylbenzoic acid methyl ester (195 mg).
MS (ES) M+H=306 and 322.

Description 25

2-Fluoro-3-(2-oxopyrrolidin-1-yl)-5-trifluoromethyl benzoic acid (D25)

2-Fluoro-3-(2-oxopyrrolidin-1-yl)-5-trifluoromethylbenzoic acid methyl ester (D24) in dioxane (10 ml) was treated with 1M LiOH solution (1.75 ml) and stirred at room temperature for 2 h. The dioxane was then removed under vacuum and dil. NaHCO₃ and ethyl acetate were added. The aqueous phase was separated, washed with ethyl acetate, acidified with 1M HCl and extracted with ethyl acetate. The organic extract was washed with brine, dried over MgSO₄ and evaporated to dryness to afford the title compound
MS (ES) M+H=292, M−H=290; and M+H=308, M−H=306

Description 26

2-Fluoro-3-(2-oxopyrrolidin-1-yl)benzoic acid methyl ester (D26)

3-Bromo-2-fluorobenzoic acid methyl ester (500 mg, 2.15 mmol) was treated with pyrrolidin-2-one (273 mg, 3.22 mmol) as described in D24 to afford the title ester (137 mg).
MS (ES) M+H=238.

Description 27

2-Fluoro-3-(2-oxopyrrolidin-1-yl)benzoic acid (D27)

2-Fluoro-3-(2-oxopyrrolidin-1-yl)benzoic acid methyl ester (D26) (137 mg, 0.58 mmol) was treated with 1M LiOH as described in D25 to afford D27 (85 mg, 66%).
MS (ES) M+H=224, M−H=222.

Description 28

(2R,4S,5S)-5-tert-Butoxycarbonylamino-4-hydroxy-2-methyl-6-phenylhexanoic acid (bicyclo[2.2.1]hept-2-yl)amide (D28)

[(S)-1-(4-Methyl-5-oxo-tetrahydrofuran-2-yl)-2-phenyl-ethyl]carbamic acid tert-butyl ester (synthesis described in Journal of Organic Chemistry (1986) 51(21), 3921) (22.2 g) was treated with (±)exo-norbornylamine (62.8 g) and the resulting mixture was heated at 70° C. overnight. The mixture was allowed to cool and poured into dil.HCl (1M; 700 ml) and extracted twice with ethyl acetate. The combined organic layers were washed with sodium bicarbonate solution, water and brine, dried and evaporated to a gummy solid. Ether was added and the mixture was stirred and then left to stand overnight. The resulting white solid precipitate was collected by filtration and dried to give D28 (14 g).

Description 29

(2R,4S,5S)-5-Amino-4-hydroxy-2-methyl-6-phenyl-hexanoic acid (bicyclo[2.2.1]hept-2-yl)amide (D29)

(2R,4S,5S)-5-tert-Butoxycarbonylamino-4-hydroxy-2-methyl-6-phenylhexanoic acid (bicyclo[2.2.1]hept-2-yl) amide (D28) (14 g) was dissolved in a solution of HCl in dioxan (4M; 220 ml) and stirred at room temperature for 2.5 h. The solution was evaporated to dryness and the residue was triturated with ether to give a white solid HCl salt. To this was added ethyl acetate and sodium bicarbonate solution and a dense white solid began to precipitate almost immediately. This was collected and dried at in vacuo 40° C. over KOH. The wet solid dried to give D29 as a white brittle foam (8.75 g).
MS (ES) M+H=331

Description 30

{(S)-1-[(2S,4R)-4-(3-Methyl-but-2-enyl)-5-oxo-tetrahydro-furan-2-yl]-2-phenyl-ethyl}carbamic acid tert-butyl ester (D30)

Prepared analogously to the synthesis of [(S)-1-(4-Methyl-5-oxo-tetrahydrofuran-2-yl)-2-phenylethyl]carbamic acid t-butyl ester in Journal of Organic Chemistry (1986) 51(21), 3921, using 4-bromo-2-methyl-2-butene in place of methyl iodide, to afford D30 in 84% yield.
¹H NMR (400 MHz, CDCl₃) 1.38 (9H, s), 1.59 (3H, s), 1.67 (3H, s), 1.92 (1H, m), 2.25 (2H, m), 2.41 (1H, m), 2.69 (1H, m), 2.89 (2H, m), 3.99 (1H, m), 4.44 (1H, m), 4.53 (1H, d J 9.7 Hz), 5.03 (1H, m) and 7.22–7.33 (5H, m).

Description 31

[(1S,2S,4R)-1-Benzyl-4-(4-bicyclo[2.2.1]hept-2-ylcarbamoyl)-2-hydroxy-7-methyl-oct-6-enyl]carbamic acid tert-butyl ester (D31)

{(S)-1-[(2S,4R)-4-(3-Methyl-but-2-enyl)-5-oxo-tetrahydro-furan-2-yl]-2-phenyl-ethyl}-carbamic acid tert-butyl ester (D30) was treated with (±)exo-norbornylamine as described in D28 to afford D31 as a white solid (60%).
MS (ES) M+H=485, M−H=483.

Description 32

[(1S,2S,4R)-1-Benzyl-4-(bicyclo[2.2.1]hept-2-ylcarbamoyl)-2-hydroxy-7-methyl-octyl]carbamic acid tert-butyl ester (D32)

[(1S,2S,4R)-1-Benzyl-4-(bicyclo[2.2.1]hept-2-ylcarbamoyl)-2-hydroxy-7-methyl-oct-6-enyl]carbamic acid tert-butyl ester (D31) (1.61 g, 3.33 mmol) in methanol (30 ml) was hydrogenated over 10% Pd/C (300 mg) for 3.75 h. The catalyst was filtered and the filtrate evaporated to afford D32 1.51 g.
MS (ES) M+H=487, M−H=485.

Description 33

(2R,4S,5S)-5-Amino-4-hydroxy-2-(3-methyl-butyl)-6-phenyl-hexanoic acid bicyclo[2.2.1]hept-2-ylamide (D33)

D33 was prepared from [(1S,2S,4R)-1-Benzyl-4-(bicyclo[2.2.1]hept-2-ylcarbamoyl)-2-hydroxy-7-methyl-octyl]carbamic acid tert-butyl ester (D32) by the method described in D29 to afford a white foam (100%).
MS (ES) M+H=387, M−H=385.

Description 34

[(S)-1-((2S,4R)-5-Oxo-4-prop-2-ynyltetrahydrofuran-2-yl)-2-phenyl-ethyl]carbamic tert-butyl ester (D34)

Prepared analogously to the starting material used in D28, using propargyl bromide (80% solution in toluene) in place of methyl iodide to afford D34 in 72% yield.
$^1$H NMR (400 MHz, CDCl$_3$) 1.38 (9H, s), 1.97 (1H, m), 2.25 (1H, m), 2.42 (1H, m), 2.55 (2H, m), 2.86 (3H, m), 4.04 (1H, m), 4.50 (1H, d J 9.7 Hz), 4.56 (1H, m) and 7.20–7.35 (5H, m).

Description 35

[(1S,2S,4R)-1-Benzyl-4-(bicyclo[2.2.1]hept-2-ylcarbamoyl)-2-hydroxy-hept-6-ynyl]-carbamic tert-butyl ester (D35)

[(S)-1-((2S,4R)-5-Oxo-4-prop-2-ynyltetrahydrofuran-2-yl)-2-phenyl-ethyl]carbamic tert-butyl ester (D34) was treated with (±)exo-norbornylamine as described in D28 to afford D35 as a white solid (84%).
MS (ES) M+H=455, M−H=453.

Description 36

(2R,4S,5S)-5-Amino-4-hydroxy-6-phenyl-2-prop-2-ynylhexanoic acid bicyclo[2.2.1]hept-2-ylamide (D36)

D36 was prepared from [(1S,2S,4R)-1-benzyl-4-(bicyclo[2.2.1]hept-2-ylcarbamoyl)-2-hydroxyhept-6-ynyl]carbamic tert-butyl ester (D35) by the method described in D29 to afford a white foam (96%).
MS (ES) M+H=355, M−H=353.

Description 37

3,5-Dibromo-2-fluorobenzoic acid (D37)

Butyllithium (1.6M solution in hexanes, 12.3 ml, 19.7 mmol) was added dropwise to a solution of 2,2,6,6-tetramethylpiperidine (3.32 ml, 19.7 mmol) in THF at −78° C. The reaction was stirred for 10 min. prior to the addition of 2,4-dibromofluorobenzene (5 g, 19.7 mmol). Stirring was continued for 2 h. The solution was then poured onto freshly crushed dry ice and allowed to warm to room temperature. The resulting solution was diluted with water (100 ml) and NaOH (2M, 10 ml) was added. This was extracted with ether (2×) and the aqueous layer was acidified to pH 1 (2M HCl) to afford a gummy solid which was triturated from ether to afford the title compound (D37) as a colourless solid (1.23 g).
$^1$H NMR (CDCl$_3$) 7.95 (1H, dd), 8.24 (1H, dd), 13.8 (1H, br s).

Description 38

Methyl 3,5-dibromo-2-fluorobenzoate (D38)

A mixture of 3,5-dibromo-2-fluorobenzoic acid (D37) (4.28 g, 14.4 mmol) and c. sulphuric acid (5 ml) in methanol (100 ml) was refluxed for 2 h. The solvent was removed under reduced pressure, the residue dissolved in ethyl acetate and washed with water, aqueous sodium bicarbonate and dried (MgSO$_4$) to afford the title compound (038) (4.06 g).
$^1$H NMR (CDCl$_3$) 3.95 (3H, s), 7.87 (1H, dd), 8.00 (1H, dd).

Description 39

Methyl 2-fluoro-3,5-bis-(2-oxopyrrolidin-1-yl)benzoate (D39)

Prepared in an analogous manner to D7 from methyl 3,5-dibromo-2-fluorobenzoate (D38).
$^1$H NMR (CDCl$_3$) 2.20 (4H, m), 2.57 (4H, m), 3.85 (4H, m), 3.93 (3H, s), 7.86 (1H, dd), 8.13 (1H, dd).

Description 40

2-Fluoro-3,5-bis-(2-oxopyrrolidin-1-yl)benzoic acid (D40)

Prepared in an analogous manner to D8 from methyl 2-fluoro-3,5-bis-(2-oxopyrrolidin-1-yl)benzoate (D39).
MS (ES) M+H=284 ($^{79}$Br), M−H=282 ($^{79}$Br).

Description 41

Methyl 3-hydroxy-5-(2-oxopyrrolidin-1-yl)-benzoate (D41)

A mixture of 3-hydroxy-5-(2-oxopyrrolidin-1-yl)benzoic acid (D6) (1.20 g, 5.43 mmol) and cesium carbonate (1.77 g, 5.43 mmol) in DMF (10 ml) was sonicated for 15 minutes. Iodomethane (0.372 ml, 5.97 mmol) was added and the mixture was stirred at room temperature. After 1 hr more iodomethane (0.05 ml) was added and stirring was continued for a further 30 minutes. The solvent was evaporated, ethyl acetate and 2N HCl were added and the product was extracted into ethyl acetate. The extracts were washed with brine, dried ($Na_2SO_4$) and concentrated. Purification by trituration with ethyl acetate and/or chromatography on silica gel (elution with ethyl acetate) gave the title compound (D41). (1.042 g).
MS (ES) M−H=234

Description 42

Methyl 3-cyclopropylmethoxy-5-(2-oxopyrrolidin-1-yl)benzoate (D42)

Prepared in an analogous manner to D14 (first part of synthesis) from cyclopropylmethanol and methyl 3-hydroxy-5-(2-oxopyrrolidin-1-yl)-benzoate (D41).
MS (ES) M+H=290.
$^1$H NMR (CDCl$_3$) 0.35 (2H, m), 0.62 (2H, m), 1.25 (1H, m), 2.17 (2H, m), 2.62 (2H, m), 3.88 (4H, m), 3.90 (3H, s), 7.36 (1H, m), 7.65 (1H, m), 7.72 (1H, m).

Description 43

Methyl 3-cyclobutyloxy-5-(2-oxopyrrolidin-1-yl)benzoate (D43)

Prepared in an analogous manner to D14 (first part of synthesis) from cyclobutanol and methyl 3-hydroxy-5-(2-oxopyrrolidin-1-yl)-benzoate (D41).
MS (ES) M+H=290.
$^1$H NMR (CDCl$_3$) 1.60–1.90 (2H, m), 2.18 (4H, m), 2.46 (2H, m), 2.59 (2H, m), 3.88 (2H, m), 3.90 (3H, s), 4.70 (1H, qn), 7.27 (1H, m), 7.60 (1H, m), 7.71 (1H, m).

Description 44

Methyl 3-((S)-sec-butyloxy)-5-(2-oxopyrrolidin-1-yl)benzoate (D44)

Prepared in an analogous manner to D14 (first part of synthesis) from (S)-sec-butanol and methyl 3-hydroxy-5-(2-oxopyrrolidin-1-yl)-benzoate (D41).
MS (ES) M+H=292.
$^1$H NMR (CDCl$_3$) 0.97 (3H, t), 1.23 (3H, d), 1.68 (2H, m), 2.19 (2H, m), 2.62 (2H, m), 3.88 (2H, m), 3.91 (3H, s), 4.38 (1H, sextet), 7.34 (1H, m), 7.61 (1H, m), 7.72 (1H, m).

Description 45

3-Cyclopropylmethoxy-5-(2-oxopyrrolidin-1-yl)benzoic acid (D45)

Prepared in an analogous manner to D8 from methyl 3-cyclopropylmethoxy-5-(2-oxopyrrolidin-1-yl)benzoate (D42).
MS (ES) M+H=276, M−H=274.

Description 46

3-Cyclobutyloxy-5-(2-oxopyrrolidin-1-yl)benzoic acid (D46)

Prepared in an analogous manner to D8 from methyl 3-cyclobutyloxy-5-(2-oxopyrrolidin-1-yl)benzoate (D43).
MS (ES) M+H=276, M−H=274.

Description 47

3-((S)sec-Butyloxy)-5-(2-oxopyrrolidin-1-yl)benzoic acid (D47)

Prepared in an analogous manner to D8 from methyl 3-((S)-sec-butyloxy)-5-(2-oxopyrrolidin-1-yl)benzoate (D44).
MS (ES) M+H=278, M−H=276.

Description 48

(3R,5S)-5-((S)-1-Amino-2-phenylethyl)-3-methyldihydrofuran-2-one (D48)

A solution of [(S)-1-(4-methyl-5-oxo-tetrahydrofuran-2-yl)-2-phenylethyl]-carbamic acid t-butyl ester (synthesis described in Journal of Organic Chemistry (1986) 51(21), 3921) (2 g, 6.27 mmol) in DCM (40 ml) was treated with trifluoroacetic acid (5 ml) for 2 h. The solvent was evaporated under reduced pressure, the residue dissolved in DCM, washed with aqueous sodium bicarbonate and dried ($Na_2SO_4$). The solvent was evaporated to afford the title compound (D48) as a pale yellow solid (1.25 g)
$^1$H NMR (CDCl$_3$) 1.28 (3H, d), 1.94 (1H, m), 2.37 (1H, m), 2.62 (1H, m), 2.84–3.02 (3H, m), 4.42 (1H, m), 2.25 (5H, m).

Description 49

3-Isopropoxy-N-[(S)-1-((2S,4R)-4-methyl-5-oxotetrahydrofuran-2-yl)-2-phenylethyl]-5-(2-oxopyrrolidin-1-yl)benzamide (D49)

Prepared in an analogous manner to D3 from 3-isopropoxy-5-(2-oxopyrrolidin-1-yl)benzoic acid (D16) and (3R,5S)-5-((S)-1-amino-2-phenylethyl)-3-methyldihydrofuran-2-one (D48).
MS (ES) M+H=465, M−H=463.

Description 50

2-Fluoro-N-[(S)-1-((2S,4R)-4-methyl-5-oxotetrahydrofuran-2-yl)-2-phenylethyl]-3,5-bis-(2-oxopyrrolidin-1-yl)benzamide (D50)

Prepared in an analogous manner to D3 from 2-fluoro-3,5-bis-(2-oxopyrrolidin-1-yl)benzoic acid (D40) and (3R,5S)-5-((S)-1-amino-2-phenylethyl)-3-methyldihydrofuran-2-one (D48).
MS (ES) M+H=508, M−H=506.

Description 51

N-[(1S,2S,4R)-1-Benzyl-4-(cyclohex-1-enylethyl-carbamoyl)-2-hydroxypentyl]-3-isopropoxy-5-(2-oxopyrrolidin-1-yl)benzamide (D51)

Prepared in an analogous manner to D1 from 2-(1-cyclohexenyl)ethylamine and 3-isopropoxy-N-[(S)-1-((2S,4R)-4-methyl-5-oxotetrahydrofuran-2-yl)-2-phenylethyl]-5-(2-oxopyrrolidin-1-yl)benzamide (D49).

MS (ES) M+H=590, M−H=588.

Description 52

4,4-Dimethylcyclohexanone oxime (D52)

A solution of sodium carbonate (10 g, 94.5 mmol) in water (30 ml) was added dropwise to a solution of 4,4-dimethylcyclohexanone (9.2 g, 73 mmol) and hydroxylamine hydrochloride (6.6 g, 94.5 mmol) in ethanol (50 ml) and water (60 ml). The resulting cloudy solution was heated at reflux for 2 h. Upon cooling the solvent volume was reduced (to remove most of the ethanol) and then extracted with ethyl acetate (2×). The organic layer was dried ($MgSO_4$) and the solvent evaporated to afford the title compound (D52) (10 g).

$^1$H NMR ($CDCl_3$) 0.99 (6H, s), 1.44 (4H, m), 2.24 (2H, m), 2.52 (2H, m), 7.46 (1H, br s).

Description 53

4,4-Dimethylcyclohexylamine (D53)

A solution of 4,4-dimethylcyclohexanone oxime (D52) (10 g) in ethanol (100 ml) was hydrogenated over Raney nickel at 50 psi for 3 days. 1M HCl in ether (100 ml) was added and the solvent removed to afford the amine as the hydrochloride salt. The title compound (D53) was liberated prior to use by dissolving in water and making strongly basic (KOH pallets), extracting with DCM (2×), drying with ($Na_2SO_4$) and evaporating the solvent carefully.

$^1$H NMR ($CDCl_3$) 0.89 (6H, s), 1.14–1.40 (6H, m), 1.62 (2H, m), 2.59 (1H, m).

Description 54 t-Butyl 2-benzylaminomethoxypyridine-4-carboxylate (D54)

t-Butyl 2-chloro-6-methoxypyridine-4-carboxylate (1.0 g) (D60) was heated in benzylamine (20 mL) for 16.5 h at 140° C. After cooling, the mixture was poured into citric acid solution (10% aq.) and extracted twice with ether. The combined extracts were washed with water and brine, dried ($MgSO_4$) and evaporated to a yellow gum. This was chromatographed on silica, eluting with hexane/ether, giving the title compound (D54) as an off-white solid (0.411 g).

$^1$H NMR ($CDCl_3$) 1.55 (9H, s), 3.85 (3H, s), 4.52 (2H, d, J=6 Hz), 4.90 (1H, br. m), 6.50 (1H, d, J=1 Hz), 6.53 (1H, d, J=1 Hz), 7.25–7.37 (5H, m).

Description 55 t-Butyl 2-amino-6-methoxypyridine-4-carboxylate (D55)

t-Butyl 2-benzylamino-6-methoxypyridine-4-carboxylate (D54) (0.294 g) in glacial AcOH (50 mL) was hydrogenated for 5 h at atmospheric pressure and room temperature in the presence of Pd—C (10%; 0.25 g). The catalyst was filtered off and washed thoroughly on the filter with MeOH. The combined filtrates were evaporated to give the title compound (D55) as a gum (0.184 g).

$^1$H NMR ($CDCl_3$) 1.56 (9H, s), 3.87 (3H, s), 4.45 (2H, br. s), 6.57 (1H, d, J=1 Hz), 6.59 (1H, d, J=1 Hz).

Description 56 t-Butyl 2-(4-bromobutyramido)-6-methoxypyridine-4-carboxylate (D56)

To a solution of t-butyl 2-amino-6-methoxypyridine-4-carboxylate (D55) (0.263 g) and pyridine (0.12 mL) in dichloromethane (16 mL) under argon, was added 4-bromobutyryl chloride (0.17 mL) dropwise (syringe). The reaction was stirred at room temp for 2.5 h and then diluted with ethyl acetate. The mixture was washed with citric acid solution (10% aq.) and the aqueous layer was re-extracted with ethyl acetate. The combined extracts were washed with aq. bicarbonate, water and brine, dried ($MgSO_4$) and evaporated to give the title compound (D56) as a pale yellow gum (0.47 g).

$^1$H NMR ($CDCl_3$) 1.58 (9H, s), 2.30 (2H, quintet, J=7 Hz), 2.63 (2H, t, J=7 Hz), 3.55 (2H, t, J=7 Hz), 3.89 (3H, s), 7.02 (1H, d, J=1 Hz), 7.82 (1H, br. s), 8.17 (1H, br. s).

Description 57 t-Butyl 2-methoxy-6-(2-oxopyrrolidin-1-yl)pyridine-4-carboxylate (D57)

t-Butyl 2-(4-bromobutyramido)-6-methoxypyridine-4-carboxylate (D56) (0.47 g) was dissolved in dioxan and treated with DBU (0.31 mL; 1 eq.). After stirring for 0.5 h, further DBU (0.31 mL; 1 eq.) was added. Stirring was continued for 2 h and the mixture was poured into citric acid solution (10% aq.) and extracted twice with ethyl acetate. The combined extracts were washed with aq. bicarbonate, water and brine, dried ($MgSO_4$) and evaporated, giving the title compound (D57) as a beige solid (0.275 g).

$^1$H NMR ($CDCl_3$) 1.59 (9H, s), 2.13 (2H, quintet, J=7 Hz), 2.67 (2H, t, J=7 Hz), 3.92 (3H, s), 4.12 (2H, t, J=7 Hz), 7.00 (1H, d, J=1 Hz), 8.41 (1H, d, J=1 Hz).

Description 58

2-Methoxy-6-(2-oxopyrrolidin-1-yl)pyridine-4-carboxylic acid (D58)

t-Butyl 2-methoxy-6-(2-oxopyrrolidin-1-yl)pyridine-4-carboxylate (D57) (0.27 g) was stirred overnight in a dioxan solution of HCl (4M; 10 mL). The solution was evaporated to dryness and dissolved in sat. aq. sodium bicarbonate. The basic aqueous solution was washed twice with ether and was then acidified to pH4 with citric acid solution (10% aq.), saturated with NaCl and extracted three times with ethyl acetate. The combined extracts were washed with brine, dried and evaporated to a solid which was triturated with water, collected by filtration and dried at 50° C. in vacuo (silica gel desiccant). The title compound (D58) was obtained as an off-white solid (0.141 g).

$^1$H NMR (DMSO-$d_6$) 2.05 (2H, quintet, J=7 Hz), 2.59 (2H, t, J=7 Hz), 3.89 (3H, s), 4.03 (2H, t, J=7 Hz), 6.91 (1H, d, J=1 Hz), 8.36 (1H, d, J=1 Hz).

Description 59

3-(4-Methoxybutoxy)-5-(2-oxopyrrolidin-1-yl)benzoic acid (D59)

A mixture of methyl 3-hydroxy-5-(2-oxopyrrolidin-1-yl) benzoate (300 mg, 11.28 mmol) (D41), polystyrene bound triphenylphosphine (1.71 g of loading 1.12 mmol/g, 1.92 mmol), and 4-methoxybutan-1-ol (200 mg, 1.92 mmol) in THF (5 ml) was treated dropwise with diethyl azodicarboxylate (0.302 ml, 1.92 mmol). The mixture was stiffed at room temperature for 6 hrs and then filtered. The resin was washed with THF and the filtrate was concentrated and chromatographed on silica gel (elution with ethyl acetate/hexane) to give methyl 3-(4-methoxybutoxy)-5-(2-oxopyrrolidin-1-yl) benzoate (280 mg).

This product was stirred in dioxan (2 ml) and 1M LiOH (2 ml) at room temperature for 2 hrs. The solvents were removed and the residue was dissolved in water and washed with ethyl acetate (2×). The aqueous solution was acidified with 2N HCl and extracted with ethyl acetate. The extracts were washed with brine, dried ($Na_2SO_4$) and concentrated to give the title compound (D59) as a white powder (236 mg)

MS (ES) M+H=348, M−H=306

Description 60 t-Butyl 2-chloro-6-methoxypyridine-4-carboxylate (D60)

2-Chloro-6-methoxypyridine-4-carboxylic acid (3.96 g) was heated in thionyl chloride (40 ml) at reflux for 2 h. The excess thionyl chloride was evaporated in vacuo and the residue was reevaporated twice with dichloromethane to give the acid chloride as an almost colourless oil (4.17 g). This was dissolved in THF (20 ml) and cooled (ice-bath). Potassium t-butoxide (2.72 g) was added. The mixture darkened and a vigorous reaction took place. Further potassium t-butoxide (1.0 g) was added and the mixture was allowed to stir at room temperature for 48 hr. The mixture was then partitioned between ethyl acetate and 10% aq. citric acid. The aqueous layer was reextracted and the combined extracts were washed with aq. bicarbonate, water and brine, dried ($MgSO_4$) and evaporated to a semi solid which was chromatographed on silica eluting with hexane/ether. The product was obtained as a colourless solid after crystallisation from hexane; and a second clean crop was obtained by recrystallisation of the material from the mother-liquors from ethanol. The total yield of the title compound (D60) was 1.53 g $^1$H NMR (DMSO-$d_6$) 1.54 (9H, s), 3.90 (3H, s), 7.16 (1H, d, J=1 Hz), 7.37 (1H, d, J=1 Hz).

Description 61

5-(4-Bromo-butanoylamino)-isophthalic acid dimethyl ester (D61)

Dimethyl 5-amino isophthalate was treated with 4-bromobutyryl chloride as described in D56 to afford D61 as a white solid (91%).

$^1$H NMR ($d_6$ DMSO) 2.13 (2H, m), 2.53 (2H, t, partially obscured by DMSO), 3.61 (2H, t, J 6.6 Hz), 3.89 (6H, s), 8.15 (1H, s), 8.50 (2H, s) and 10.42 (1H, s).

MS (ES) M+H=358.

Description 62

5-(2-Oxo-pyrrolidin-1-yl)-isophthalic acid dimethyl ester (D62)

5-(4-Bromo-butanoylamino)-isophthalic acid dimethyl ester (D61) was treated with DBU as described in D57 to afford D62 as a white solid (35%).

$^1$H NMR ($d_6$ DMSO) 2.11 (2H, m), 2.56 (2H, t, partially obscured by DMSO), 3.92 (6H, s), 3.95 (2H, t), 8.23 (1H, s) and 8.47 (2H, s).

MS (ES) M+H=278.

Description 63

5-(2-Oxo-pyrrolidin-1-yl)-isophthalic acid monomethyl ester (D63)

5-(2-Oxo-pyrrolidin-1-yl)-isophthalic acid dimethyl ester (D62) (3.92 g, 14.14 mmol) was dissolved in methanol (133 ml) and treated with 1M NaOH soln. (15.6 ml, 15.6 mmol). The resulting solution was stirred at room temperature for 3 h. The methanol was then removed under vacuum, the aqueous residue was treated with dil. $NaHCO_3$ soln. and then washed with EtOAc (some insoluble, unreacted starting material was filtered off). The aqueous soln. was then acidified to pH1 with 2M HCl and the product was extracted into EtOAc (×3). The combined extracts were washed with brine, dried ($MgSO_4$) and evaporated to leave the product as a white solid (1.9 g, 51%). LC/MS of the product showed the title compound (D63) and a trace of the corresponding di-acid.

MS (ES) M+H=264 and M−H⁻=262. (Also showed some di-acid M+H=250 and M−H⁻=248.)

Description 64

N-Methyl-5-(2-oxo-pyrrolidin-1-yl)-N-propyl-isophthalamic acid methyl ester (D64)

5-(2-Oxo-pyrrolidin-1-yl)-isophthalic acid monomethyl ester (D63) (1.0 g, 3.8 mmol) was dissolved in DMF (7 ml) and treated with N-methyl propylamine (0.42 g, 5.7 mmol), HOBt (0.62 g, 4.56 mmol) and EDC (1.02 g, 5.32 mmol) and the resulting solution was stirred overnight at room temperature. It was then evaporated to dryness and the residue was partitioned between EtOAc and dil.HCl. The organic phase was separated, washed with dil.HCl (×2), dil.$NaHCO_3$ (×3) and brine (×1). It was dried ($MgSO_4$) and evaporated to leave the crude product which was purified by silica chromatography eluting with DCM/MeOH to afford the pure title compound (D64) (0.40 g, 33%).

$^1$H NMR ($CDCl_3$) (rotamers were evident) 0.79 and 0.99 (3H, 2×t), 1.60 and 1.70 (2H, 2×m), 2.20 (2H, m), 2.64 (2H, t, J 8.0), 2.97 and 3.08 (3H, 2×s), 3.25 and 3.49 (2H, 2×m), 3.92 (5H, m), 7.85 (1 h, s), 8.08 (1H, br.s) and 8.15 (1H, s).

MS (ES) M+H=319.

Description 65

N-Methyl-5-(2-oxo-pyrrolidin-1-yl)-N-propyl-isophthalamic acid (D65)

N-Methyl-5-(2-oxo-pyrrolidin-1-yl)-N-propyl-isophthalamic acid methyl ester (D64) (0.40 g, 1.25 mmol) in dioxane (15 ml) was treated with 1M LiOH (2.5 ml, 2.5 mmol) and the reaction solution was stirred at room temperature for 2 h. It was then evaporated to dryness and the residue was partitioned between EtOAc and dil. NaHCO₃ soln. The aqueous solution was separated and acidified to pH1 with 2M HCl. The product was extracted into EtOAc (×3) and the combined extracts were washed with brine, dried over MgSO₄ and evaporated to afford the title compound (D65) (0.30 g, 79%).

MS (ES) M+H=305 and M−H⁻=303.

Example 1

N-[(1S,2S,4R)-1-Benzyl-4-(3,3-dimethylbutylcarbamoyl)-2-hydroxypentyl]-4-fluoro-3-(2-oxopyrrolidin-1-yl)-benzamide (E1)

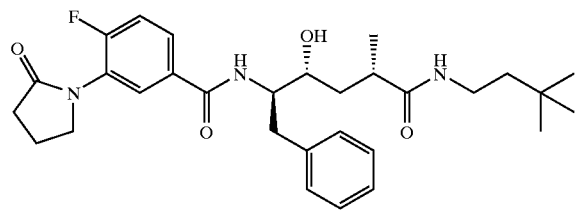

A mixture of N-[(1S,2S,4R)-1-benzyl-4-(3,3-dimethylbutylcarbamoyl)-2-hydroxypentyl]-3-bromo-4-fluoro-benzamide (126 mg, 0.24 mmol) (D3), caesium carbonate (117 mg, 0.36 mmol), 2-pyrrolidinone (1 ml of 0.36M solution in 1,4-dioxan, 0.36 mmol), 9,9-dimethyl-4,5-bis(diphenylphosphino)xanthene (1 ml of 0.015M solution in 1,4-dioxan) and tris(dibenzylideneacetone)dipalladium (0) (1 ml of 0.005M solution in 1,4-dioxan, 0.01 mmol of Pd) was refluxed under argon for 40 h. After cooling, the mixture was filtered and evaporated in vacuo. Column chromatography on silica gel (elution with dichloromethane/methanol) gave the title compound (52 mg) as a white solid.

MS (ES) MH⁺=526, M−H⁻=524

¹H NMR (400 MHz, DMSO-d₆): 0.84 (9H, s), 0.97 (3H, d, J 7.0 Hz), 1.24 (3H, m), 1.74 (1H, m), 2.14 (2H, m), 2.50 (3H, m, partially obscured by solvent), 2.78–3.00 (4H, series of m), 3.45 (1H, m), 3.78 (2H, m), 4.13 (1H, m), 4.83 (1H, d, J 6.0 Hz), 7.12 (1H, t, J 7.0 Hz), 7.23 (4H, m), 7.37 (1H, dd, J 9.0, 10.0 Hz), 7.58 (1H, t, J 5.5 Hz), 7.77 (1H, m), 7.86 (1H, dd, J 2.0, 7.5 Hz), 8.09 (1H, d, J 9.0 Hz).

Example 2

N-[(1S,2S,4R)-1-Benzyl-4-(3,3-dimethylbutylcarbamoyl)-2-hydroxypentyl]-3-hydroxy-5-(2-oxopyrrolidin-1-yl)-benzamide (E2)

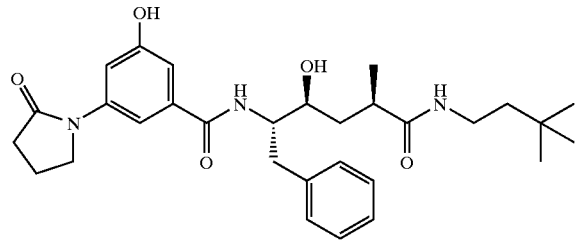

To a stirred solution of 3-hydroxy-5-(2-oxopyrrolidin-1-yl)benzoic acid (D6) (0.449 g, 2.03 mmol), EDC (0.389 g, 2.03 mmol) and HOBT (0.311 g, 2.03 mmol) in DMF (8 ml) was added (2R,4S,5S)-5-amino-4-hydroxy-2-methyl-6-phenylhexanoic acid (3,3-dimethylbutyl)amide (D2(0.50 g, 1.56 mmol). After stirring for 20 hrs at room temperature, the DMF was evaporated and ethyl acetate and water were added. The product was extracted into ethyl acetate and the combined extracts were washed with 2N HCl, saturated aqueous sodium bicarbonate solution and brine and then dried over sodium sulfate and evaporated. Purification by column chromatography on silica gel (elution with 2–5% methanol in dichloromethane) gave the product, 0.588 g.

MS (ES) MH⁺=524.

Example 3

3-Allyloxy-N-[(1S,2S,4R)-1-benzyl-4-(3,3-dimethylbutylcarbamoyl)-2-hydroxypentyl]-5-(2-oxopyrrolidin-1-yl)-benzamide (E3)

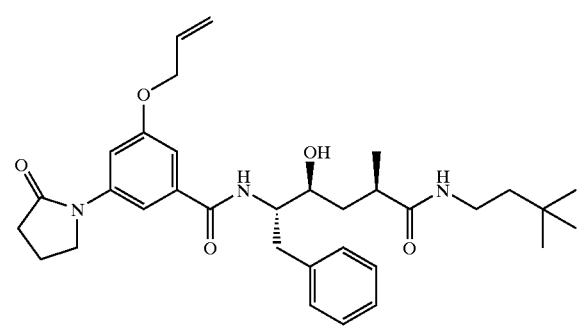

A mixture of N-[(1S,2S,4R)-1-Benzyl-4-(3,3-bimethylbutylcarbamoyl)-2-hydroxypentyl]-3-hydroxy-5-(2-oxopyrrolidin-1-yl)-benzamide (E2) (0.061 g, 0.117 mmol), caesium carbonate (0.050 g, 0.152 mmol) and allyl bromide (0.016 ml, 0.176 mmol) in DMF (1 ml) was stirred vigorously at room temperature for 2 hrs. More allyl bromide (0.008 ml) was added and stirring was continued for a further 1 hr. The mixture was diluted with ethyl acetate and 2N HCl and the product was extracted into ethyl acetate. The combined extracts were washed with brine, dried over sodium sulfate and evaporated. Purification by column chromatography on silica gel (elution with 2–5% methanol in dichloromethane) gave the product, 0.047 g.

MS (ES) MH⁺=564

Example 4

N-[(1S,2S,4R)-1-Benzyl-4-(3,3-dimethylbutylcarbamoyl)-2-hydroxypentyl]-3-(2-oxopyrrolidin-1-yl)-5-propoxybenzamide (E4)

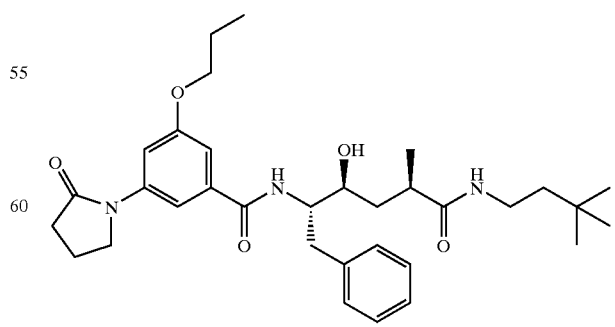

The allyl compound of E3 (0.042 g) was hydrogenated in methanol (5 ml) in the presence of 5% palladium-barium sulfate (0.020 g) for 3 hrs. The mixture was filtered through celite and evaporated to give the title compound.

MS (ES) MH+=566

$^1$H NMR (DMSO-d$_6$) 0.84 (9H, s), 0.98 (6H, m), 1.24 (3H, m), 1.75 (3H, m), 2.06 (2H, m), 2.50 (3H, m, obscured by solvent), 2.80–3.05 (4H, series of m), 3.47 (1H, m), 3.85 (2H, m), 3.96 (2H, t, J=6.5 Hz), 4.12 (1H, m), 4.90 (1H, broad), 7.12 (2H, m), 7.25 (4H, m), 7.40 (1H, s), 7.55 (1H, s), 7.59 (1H, m), 8.05 (1H, d, J 9.0 Hz)

Example 5

N-[(1S,2S,4R)-1-Benzyl-4-(3,3-dimethyl-butylcarbamoyl)-2-hydroxypenyl]-3,5-bis-(2-oxo-pyrrolidin-1-yl)benzamide (E5)

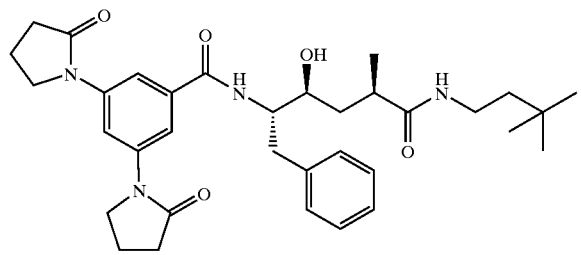

To a solution of (2R,4S,5S)-5-amino-4-hydroxy-2-methyl-6-phenylhexanoic acid (3,3-dimethylbutyl)amide (D2) (46 mg, 0.145 mmol) in DMF (2 ml) was added iPr$_2$NEt (61 μl, 0.348 mmol) followed by 3,5-bis-2-oxopyrrolidin-1-yl)benzoic acid (D8) (50 mg, 0.174 mmol) and HATU (77 mg, 0.203 mmol). The reaction mixture was stirred at room temperature for 6 hours. The solvent was evaporated to dryness and the residue was partitioned between 0.5 M HCl and DCM. The organic phase was separated and washed with NaHCO$_3$, brine and dried over MgSO$_4$, filtered and evaporated to afford the crude product (61 mg) as yellow oil. The product was triturated in petroleum/diethylether which yielded E5 (55 mg) as a yellow solid.

MS (ES) M+H=591, M–H=589.

Example 6

N-[(1S,2S,4R)-1-Benzyl-4-(3,3-dimethylbutylcarbamoyl)-2-hydroxypentyl]-3-(2-oxopyrrolidin-1-yl)-5-phenylbenzamide (E6)

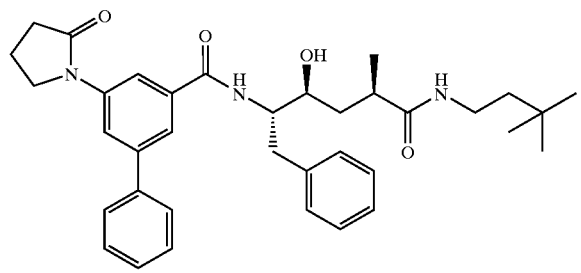

Polystyrene linked carbodiimide (21 mg, 1.7 mmol/g, 0.036 mmol) was placed in a vial with DCM (1 ml). To this was added HOBT (5 mg, 0.036 mmol) in 1 ml DCM/DMF=4:1, 5-(2-oxo-pyrrolidin-1-yl)-biphenyl-3-carboxylic acid (D11) (10 mg, 0.036 mmol) in 1 ml DCM/DMF=4:1, and (2R,4S,5S)-5-amino-4-hydroxy-2-methyl-6-phenylhexanoic acid (3,3-dimethylbutyl)amide (D2) (in 1 ml DCM). The mixture was stirred at room temperature overnight. Scavenger resins trisamine (~100 mg) and isocyanate (~100 mg) were added and the mixture was stirred for another 1.5 hours. The resins were filtered and the solvent evaporated in vacuo. Column chromatography on silica gel (5% MeOH in DCM) gave E6 (5 mg).

MS (ES) M+H=584, M–H=582.

Example 7

N-[(1S,2S,4R)-1-Benzyl-4-(bicyclo[2.2.1]hept-2-ylcarbamoyl)-2-hydroxy-7-methyloctyl]-3,5-bis-(2-oxo-pyrrolidin-1-yl)benzamide (E7)

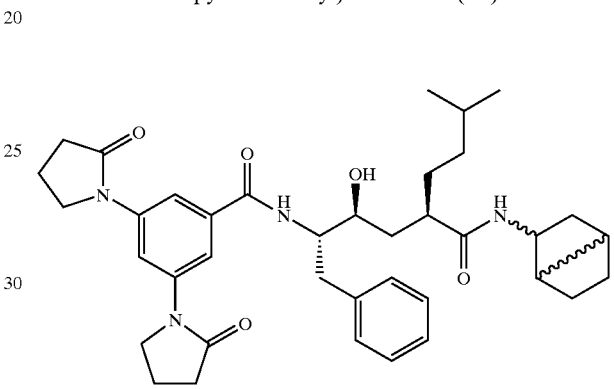

Prepared in an analogous manner to E6 from 3,5-bis-(2-oxopyrrolidin-1-yl)benzoic acid (D8) and (2R,4S,5S)-5-amino-4-hydroxy-2-(3-methyl-butyl)-6-phenyl-hexanoic acid bicyclo[2.2.1]hept-2-ylamide (D33).

MS (ES) M+H=657, M–H=655.

Example 8

N-[(1S,2S,4R)-1-Benzyl-4-(bicyclo[2.2.1]hept-2-ylcarbamoyl)-2-hydroxypentyl]-3,5-bis-(2-oxopyrrolidin-1-yl)benzamide (E8)

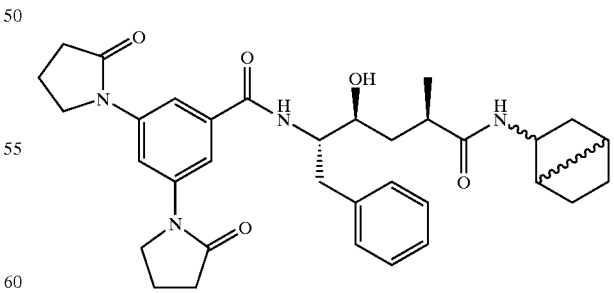

Prepared in an analogous manner to E6, from 3,5-bis-(2-oxopyrrolidin-1-yl)benzoic acid (D8) and (2R,4S,5S)-5-amino-4-hydroxy-2-methyl-6-phenylhexanoic acid (bicyclo[2.2.1]hept-2-yl)amide (D29).

MS (ES) M+H=601, M–H=599.

Example 9

N-[(1S,2S,4R)-1-Benzyl-4-(bicyclo[2.2.1]hept-2-ylcarbamoyl)-2-hydroxyhept-6-ynyl]-3,5-bis-(2-oxopyrrolidin-1-yl)benzamide (E9)

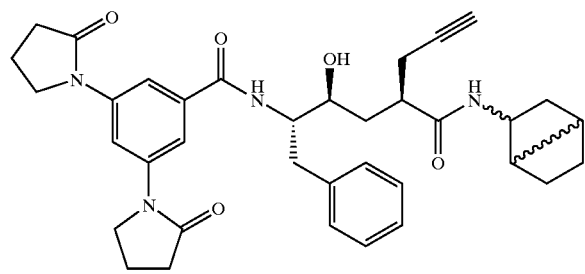

Prepared in an analogous manner to E5 from 3,5-bis-(2-oxopyrrolidin-1-yl)benzoic acid (D8) and (2R,4S,5S)-5-amino-4-hydroxy-6-phenyl-2-prop-2-ynylhexanoic acid bicyclo[2.2.1]hept-2-ylamide (D36).

MS (ES) M+H=625, M−H=623.

Example 10

3-Acetylamino-N-[(1S,2S,4R)-1-benzyl-4-(bicyclo[2.2.1]hept-2-ylcarbamoyl)-2-hydroxypentyl]-5-(2-oxopyrrolidin-1-yl)benzamide (E10)

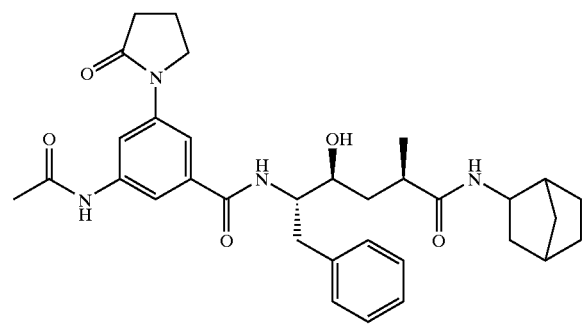

Prepared in an analogous manner to E5, from 3-acetylamino-5-(2-oxopyrrolidin-1-yl)benzoic acid (D13) and (2R,4S,5S)-5-amino-4-hydroxy-2-methyl-6-phenylhexanoic acid (bicyclo[2.2.1]hept-2-yl)amide (D29).

MS (ES) M+H=575, M−H=573.

Example 11

N-[(1S,2S,4R)-1-Benzyl-4-(3,3-dimethylbutylcarbamoyl)-2-hydroxypentyl]-3-(2-oxopyrrolidin-1-yl)-5-phenoxybenzamide (E11)

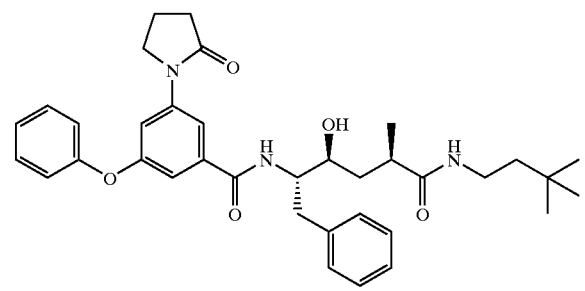

A mixture of N-[(1S,2S,4R)-1-benzyl-4-(3,3-dimethylbutylcarbamoyl)-2-hydroxypentyl]-3-hydroxy-5-(2-oxopyrrolidin-1-yl)benzamide (E2) (52 mg, 0.1 mmol), benzeneboronic acid (25 mg, 0.2 mmol), cupric acetate (18 mg, 0.1 mmol) and powdered 4 A molecular sieves in dichloromethane (1 ml) were treated with triethylamine (0.070 ml, 0.5 mmol). After stirring for 40 hrs at room temperature, the mixture was partitioned between ethyl acetate and 2N HCl and the product was extracted into ethyl acetate. The extracts were washed with sodium bicarbonate solution and brine and then dried (Na$_2$SO$_4$) and concentrated. Chromatography on silica gel (elution with ethyl acetate) gave E11 as a white solid (24 mg).

MS (ES+), M+H=600

Example 12

N-[(1S,2S,4R)-1-Benzyl-4-bicyclo[2.2.1]hept-2-ylcarbamoyl)-2-hydroxypentyl]-3-(3-methoxypropoxy)-5-(2-oxopyrrolidin-1-yl)benzamide (E12)

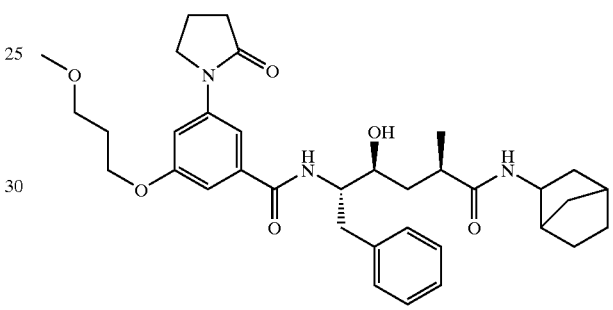

Prepared in an analogous manner to E6 from 3-(3-methoxypropoxy)-5-(2-oxopyrrolidin-1-yl)benzoic acid (D14) and (2R,4S,5S)-5-amino-4-hydroxy-2-methyl-6-phenylhexanoic acid (bicyclo[2.2.1]hept-2-yl)amide (D29).

MS (ES+), M+H=606

Example 13

N-[(1S,2S,4R)-1-Benzyl-4-bicyclo[2.2.1]hept-2-ylcarbamoyl)-2-hydroxypentyl]-3-(2-hydroxyethoxy)-5-(2-oxopyrrolidin-1-yl)benzamide (E13)

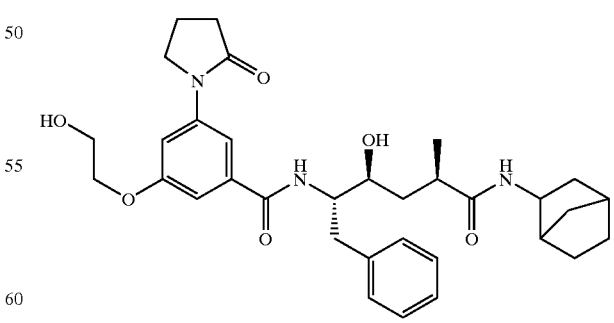

Prepared in an analogous manner to E6, from 3-(2-hydroxyethoxy)-5-(2-oxopyrrolidin-1-yl)benzoic acid (D15) and (2R,4S,5S)-5-amino-4-hydroxy-2-methyl-6-phenylhexanoic acid (bicyclo[2.2.1]hept-2-yl)amide (D29).

MS (ES+), M+H=578

Example 14

N-[(1S,2S,4R)-1-Benzyl-4-(bicyclo[2.2.1]hept-2-ylcarbamoyl)-2-hydroxypentyl]-3-isopropoxy-5-(2-oxopyrrolidin-1-yl)benzamide (E14)

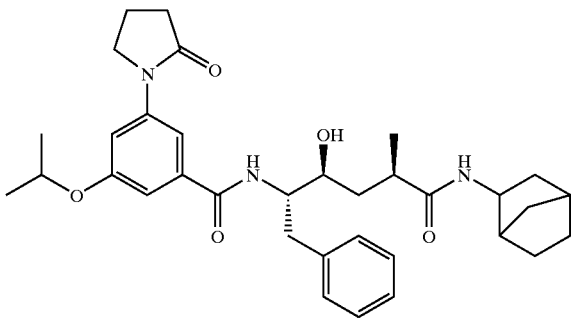

Prepared in an analogous manner to E6 from 3-isopropoxy-5-(2-oxopyrrolidin-1-yl)benzoic acid (D16) and (2R,4S,5S)-5-amino-4-hydroxy-2-methyl-6-phenylhexanoic acid (bicyclo[2.2.1]hept-2-yl)amide (D29).
MS (ES+), M+H=576

Example 15

N-[(1S,2S,4R)-1-Benzyl-4-(bicyclo[2.2.1]hept-2-ylcarbamoyl)-2-hydroxy-pentyl]-3-methoxy-5-(2-oxopiperidin-1-yl)benzamide (E15)

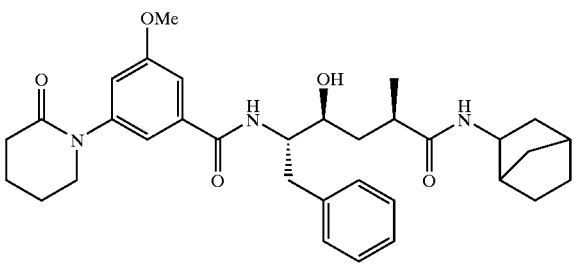

Prepared in an analogous manner to E1, from N-[(1S,2S,4R)-1-benzyl-4-(3,3-dimethylbutylcarbamoyl)-2-hydroxypentyl]-3-bromo-5-methoxybenzamide (D17) and δ-valerolactam.
MS (ES) M+H=562, M−H=560

Example 16

N-[(1S,2S,4R)-1-Benzyl-4-(bicyclo[2.2.1]hept-2-ylcarbamoyl)-2-hydroxypentyl]-3-methoxy-5-(2-oxoazepan-1-yl)benzamide (E16)

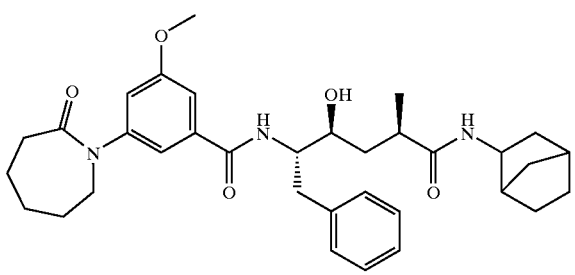

Prepared in an analogous manner to E1, from N-[(1S,2S,4R)-1-benzyl-4-(3,3-dimethylbutylcarbamoyl)-2-hydroxypentyl]-3-bromo-5-methoxybenzamide (D17) and ε-caprolactam.
MS (ES) M+H=576, M−H=574.

Example 17

N-[(1S,2S,4R)-1-Benzyl-4-(bicyclo[2.2.1]hept-2-ylcarbamoyl)-2-hydroxypentyl]-3-(2-oxooxazolidin-3-yl)benzamide (E17)

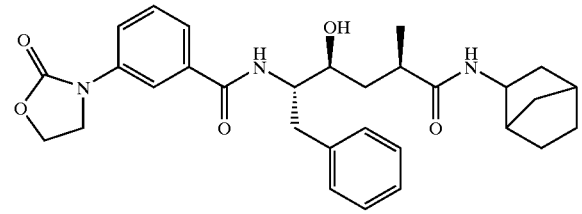

Prepared in an analogous manner to E6, from 3-(2-oxooxazolidin-3-yl)benzoic acid (D19) and (2R,4S,5S)-5-amino-4-hydroxy-2-methyl-6-phenylhexanoic acid (bicyclo[2.2.1]hept-2-yl)amide (D29).
MS (ES) M+H=520, M−H=518.

Example 18

N-[(1S,2S,4R)-1-Benzyl-4-(bicyclo[2.2.1]hept-2-ylcarbamoyl)-2-hydroxypentyl]-3-((R)-4-benzyl-2-oxooxazolidin-3-yl)benzamide (E18)

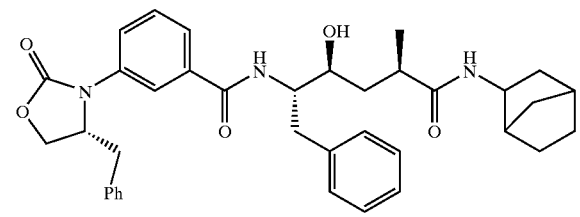

Prepared in an analogous manner to E6 from 3-((R)-4-benzyl-2-oxooxazolidin-3-yl)benzoic acid (D21) and (2R,4S,5S)-5-amino-4-hydroxy-2-methyl-6-phenylhexanoic acid (bicyclo[2.2.1]hept-2-yl)amide (D29).
MS (ES) M+H=610, M−H=608.

Example 19

N-[(1S,2S,4R)-1-Benzyl-4-(bicyclo[2.2.1]hept-2-ylcarbamoyl)-2-hydroxy-pentyl]-3-((S)-4-isopropyl-2-oxo-oxazolidin-3-yl)-benzamide (E19)

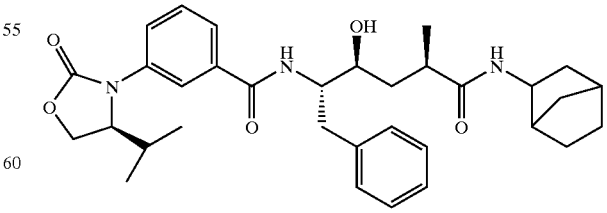

Prepared in an analogous manner to E6 from 3-((S)-4-isopropyl-2-oxo-oxazolidin-3-yl)benzoic acid (D23) and (2R,4S,5S)-5-amino-4-hydroxy-2-methyl-6-phenylhexanoic acid (bicyclo[2.2.1]hept-2-yl)amide (D29).
MS (ES) M+H=562, M−H=560.

Example 20

N-[(1S,2S,4R)-1-Benzyl-4-(bicyclo[2.2.1]hept-2-ylcarbamoyl)-2-hydroxypentyl]-2-fluoro-3-(2-oxopyrrolidin-1-yl)-5-trifluoromethyl-benzamide (E20)

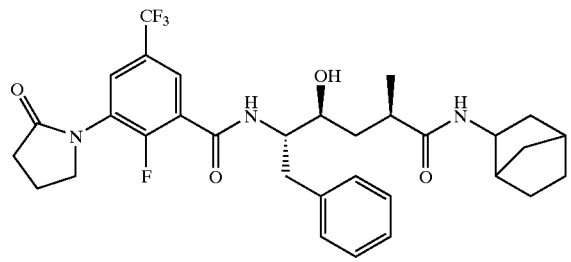

Prepared in an analogous manner to E6 from 2-fluoro-3-(2-oxopyrrolidin-1-yl)-5-trifluoromethyl benzoic acid (D25) and (2R,4S,5S)-5-amino-4-hydroxy-2-methyl-6-phenylhexanoic acid (bicyclo[2.2.1]hept-2-yl)amide (D29).

MS (ES) M+H=604, M−H=602.

Example 21

N-[(1S,2S,4R)-1-Benzyl-4-(bicyclo[2.2.1]hept-2-ylcarbamoyl)-2-hydroxypentyl]-2-fluoro-3-(2-oxopyrrolidin-1-yl)-benzamide (E21)

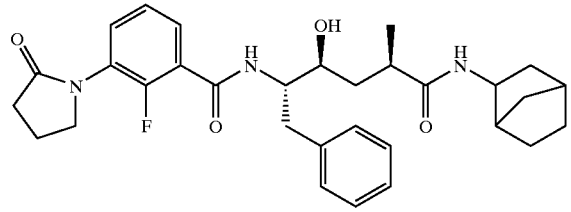

Prepared in an analogous manner to E6 from 2-fluoro-3-(2-oxopyrrolidin-1-yl)benzoic acid (D27) and (2R,4S,5S)-5-amino-4-hydroxy-2-methyl-6-phenylhexanoic acid (bicyclo[2.2.1]hept-2-yl)amide (D29).

MS (ES) M+H=536, M−H=534.

Example 22

N-[(1S,2S,4R)-1-Benzyl-4-(bicyclo[2.2.1]hept-2-ylcarbamoyl)-2-hydroxypentyl]-2-fluoro-3,5-bis-(2-oxopyrrolidin-1-yl)benzamide (E22)

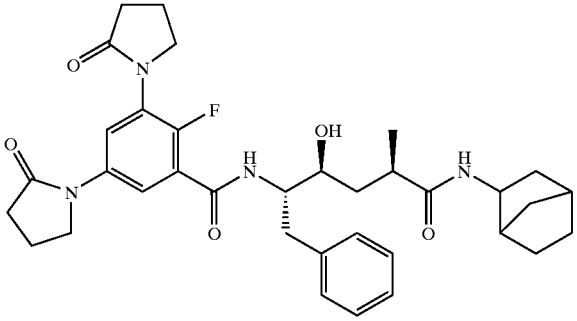

Prepared in an analogous manner to E6 from 2-fluoro-3,5-bis-(2-oxopyrrolidin-1-yl)benzoic acid (D40) and (2R,4S,5S)-5-amino-4-hydroxy-2-methyl-6-phenylhexanoic acid (bicyclo[2.2.1]hept-2-yl)amide (D29).

MS (ES) M+H=619, M−H=617.

Example 23

N-[(1S,2S,4R)-1-Benzyl-4-(bicyclo[2.2.1]hept-2-ylcarbamoyl)-2-hydroxypentyl]-3-cyclopropylmethoxy-5-(2-oxopyrrolidin-1-yl)benzamide (E23)

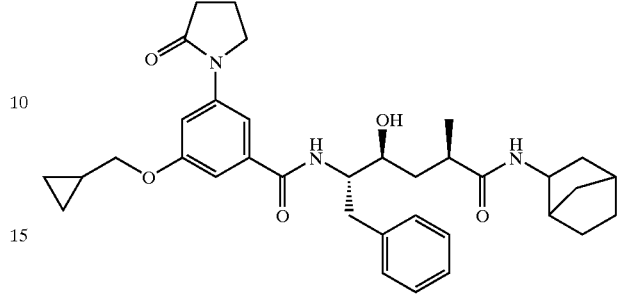

Prepared in an analogous manner to E6 from 3-cyclopropylmethoxy-5-(2-oxopyrrolidin-1-yl)benzoic acid (D45) and (2R,4S,5S)-5-amino-4-hydroxy-2-methyl-6-phenylhexanoic acid (bicyclo[2.2.1]hept-2-yl)amide (D29).

MS (ES) M+H=588, M−H=586.

Example 24

N-[(1S,2S,4R)-1-Benzyl-4-(bicyclo[2.2.1]hept-2-ylcarbamoyl)-2-hydroxypentyl]-3-cyclobutoxy-5-(2-oxopyrrolidin-1-yl)benzamide (E24)

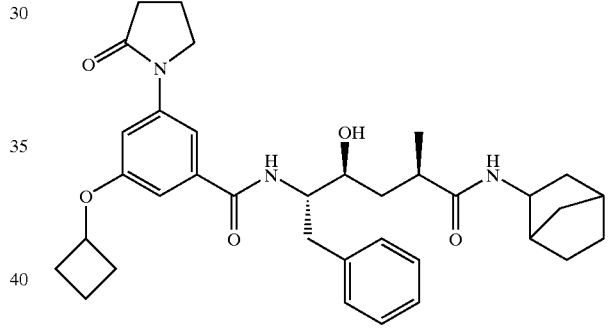

Prepared in an analogous manner to E6 from 3-cyclobutyloxy-5-(2-oxopyrrolidin-1-yl)benzoic acid (D46) and (2R,4S,5S)-5-amino-4-hydroxy-2-methyl-6-phenylhexanoic acid (bicyclo[2.2.1]hept-2-yl)amide (D29).

MS (ES) M+H=588, M−H=586.

Example 25

N-[(1S,2S,4R)-1-Benzyl-4-(bicyclo[2.2.1]hept-2-ylcarbamoyl)-2-hydroxypentyl]-3-((S)-sec-butoxy)-5-(2-oxopyrrolidin-1-yl)benzamide (E25)

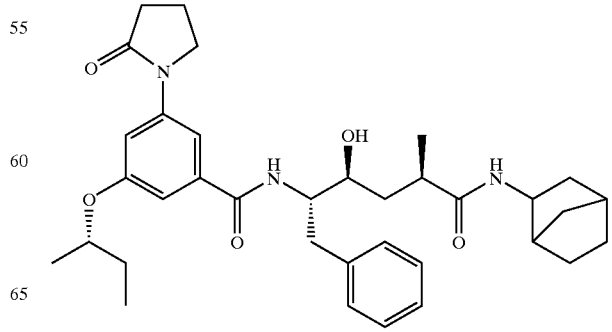

Prepared in an analogous manner to E6 from 3-((S)-sec-butyloxy)-5-(2-oxopyrrolidin-1-yl)benzoic acid (D47) and (2R,4S,5S)-5-amino-4-hydroxy-2-methyl-6-phenylhexanoic acid (bicyclo[2.2.1]hept-2-yl)amide (D29).
MS (ES) M+H=590, M−H=588.

Example 26

N-[(1S,2S,4R)-1-Benzyl-4-(cyclobutylcarbamoyl)-2-hydroxypentyl]-3-isopropoxy-5-(2-oxopyrrolidin-1-yl)benzamide (E26)

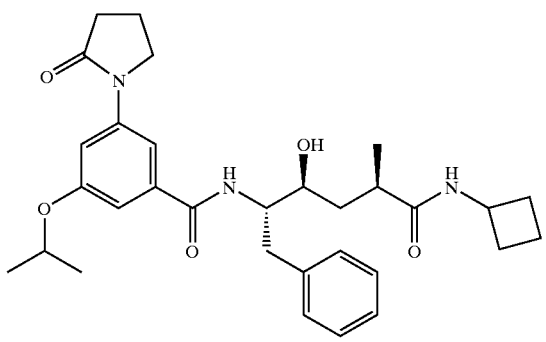

Prepared in an analogous manner to D1 from cyclobutylamine and 3-isopropoxy-N-[(S)-1-((2S,4R)-4-methyl-5-oxotetrahydrofuran-2-yl)-2-phenylethyl]-5-(2-oxopyrrolidin-1-yl)benzamide (D49).
MS (ES) M+H=536, M−H=534.

Example 27

N-[(1S,2S,4R)-1-Benzyl-4-(isobutylcarbamoyl)-2-hydroxypentyl]-3-isopropoxy-5-(2-oxopyrrolidin-1-yl)benzamide (E27)

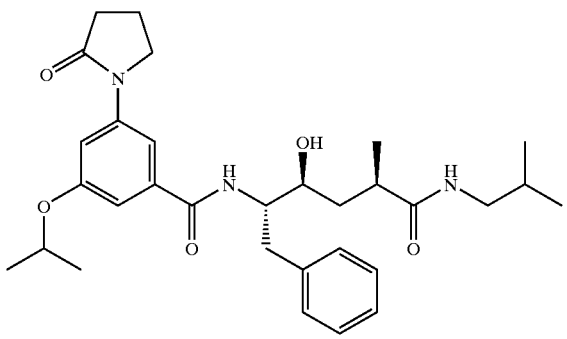

Prepared in an analogous manner to D1 from isobutylamine and 3-isopropoxy-N-[(S)-1-((2S,4R)-4-methyl-5-oxotetrahydrofuran-2-yl)-2-phenylethyl]-5-(2-oxopyrrolidin-1-yl)benzamide (D49).
MS (ES) M+H=538, M−H=536.

Example 28

N-[(1S,2S,4R)-1-Benzyl-4-(cyclopropylmethylcarbamoyl)-2-hydroxypentyl]-3-isopropoxy-5-(2-oxopyrrolidin-1-yl)benzamide (E28)

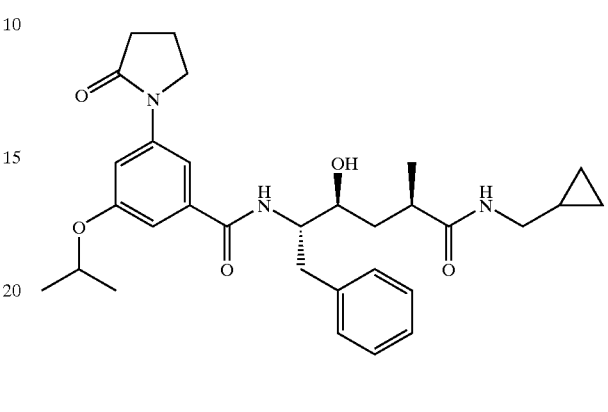

Prepared in an analogous manner to D1 from cyclopropylmethylamine and 3-isopropoxy-N-[(S)-1-((2S,4R)-4-methyl-5-oxotetrahydrofuran-2-yl)-2-phenylethyl]-5-(2-oxopyrrolidin-1-yl)benzamide (D49).
MS (ES) M+H=536, M−H=534.

Example 29

N-[(1S,2S,4R)-1-Benzyl-4-(4,4-dimethylcyclohexylcarbamoyl)-2-hydroxypentyl]-3-isopropoxy-5-(2-oxopyrrolidin-1-yl)benzamide (E29)

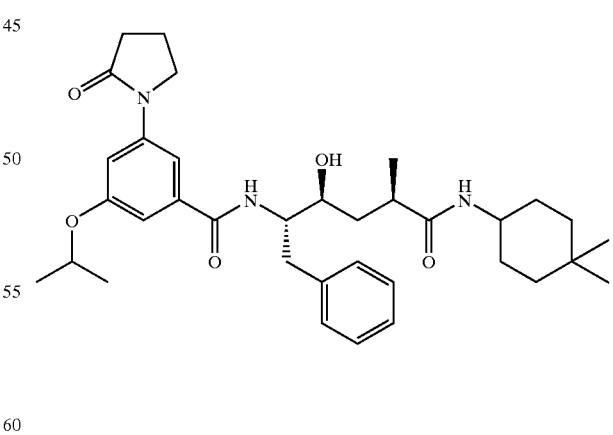

Prepared in an analogous manner to D1 from 4,4-dimethylcyclohexylamine (D53) and 3-isopropoxy-N-[(S)-1-((2S,4R)-4-methyl-5-oxotetrahydrofuran-2-yl)-2-phenylethyl]-5-(2-oxopyrrolidin-1-yl)benzamide (D49).
MS (ES) M+H=592, M−H=590.

Example 30

N-[(1S,2S,4R)-1-Benzyl-4-(2-cyclohexylethylcarbamoyl)-2-hydroxypentyl]-3-isopropoxy-5-(2-oxopyrrolidin-1-yl)benzamide (E30)

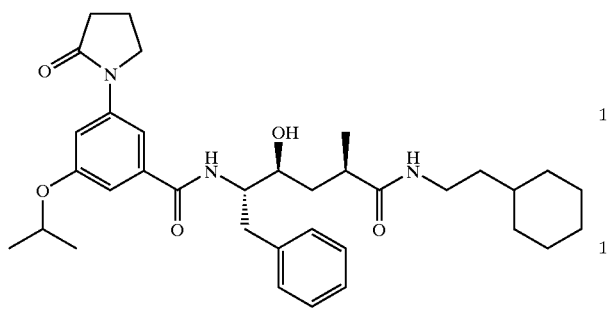

Prepared in an analogous manner to D6 (hydrogenation stage) from N-[(1S,2S,4R)-1-benzyl-4-(cyclohex-1-enylethylcarbamoyl)-2-hydroxypentyl]-3-isopropoxy-5-(2-oxopyrrolidin-1-yl)benzamide (D51).
MS (ES) M+H=592, M−H=590.

Example 31

N-[(1S,2S,4R)-1-Benzyl-4-(cyclobutylcarbamoyl)-2-hydroxypentyl]-2-fluoro-3,5-bis-(2-oxopyrrolidin-1-yl)benzamide (E31)

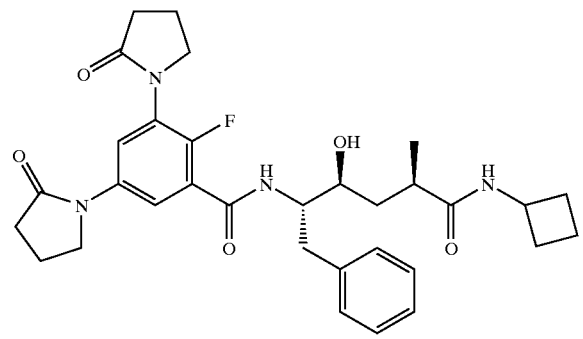

Prepared in an analogous manner to D1 from cyclobutylamine and 2-fluoro-N-[(S)-1-((2S,4R)-4-methyl-5-oxotetrahydrofuran-2-yl)-2-phenylethyl]-3,5-bis-(2-oxopyrrolidin-1-yl)benzamide (D50).
MS (ES) M+H=579, M−H=577.

Example 32

N-[(1S,2S,4R)-1-Benzyl-4-(4-tert-butylcyclohexylcarbamoyl)-2-hydroxypentyl]-2-fluoro-3,5-bis-(2-oxopyrrolidin-1-yl)benzamide (E32)

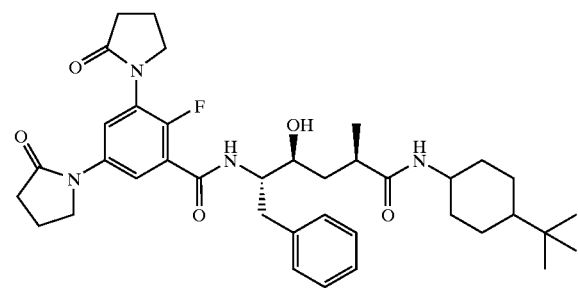

Prepared in an analogous manner to D1 from 4-tert-butylcyclohexylamine and 2-fluoro-N-[(S)-1-((2S,4R)-4-methyl-5-oxotetrahydrofuran-2-yl)-2-phenylethyl]-3,5-bis-(2-oxopyrrolidin-1-yl)benzamide (D50).
MS (ES) M+H=663, M−H=661.

Example 33

N-[(1S,2S,4R)-1-Benzyl-4-(bicyclo[2.2.1]hept-2-ylcarbamoyl)-2-hydroxy-pentyl]-N'-methyl-5-(2-oxo-pyrrolidin-1-yl)-N'-propyl-isophthalamide (E33)

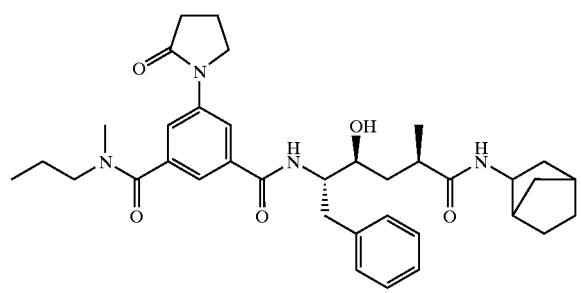

Prepared in an analogous manner to E6, from N-methyl-5-(2-oxo-pyrrolidin-1-yl)-N-propyl-isophthalamic acid (D65) and (2R,4S,5S)-5-amino-4-hydroxy-2-methyl-6-phenylhexanoic acid (bicyclo[2.2.1]hept-2-yl)amide (D29).
MS (ES) M+H=617, M−H=615.

Example 34

N-[(1S,2S,4R)-1-Benzyl-4-(bicyclo[2.2.1]hept-2-ylcarbamoyl)-2-hydroxypentyl]-2-methoxy-6-(2-oxopyrrolidin-1-yl)pyridine-4-carboxamide (E34)

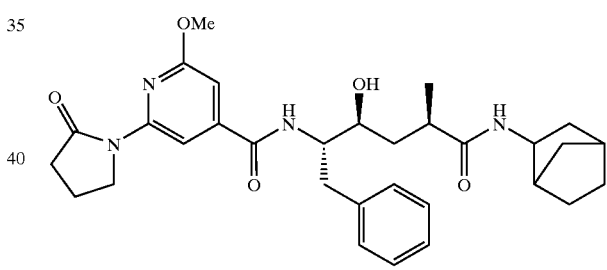

Prepared in an analogous manner to E6, from 2-methoxy-6-(2-oxopyrrolidin-1-yl)pyridine-4-carboxylic acid (D58) and (2R,4S,5S)-5-amino-4-hydroxy-2-methyl-6-phenylhexanoic acid (bicyclo[2.2.1]hept-2-yl)amide (D29).
MS (ES) MH$^+$=549

Example 35

N-[(1S,2S,4R)-1-Benzyl-4-(bicyclo[2.2.1]hept-2-ylcarbamoyl)-2-hydroxypentyl]-3-(4-methoxybutoxy)-5-(2-oxopyrrolidin-1-yl)benzamide (E35)

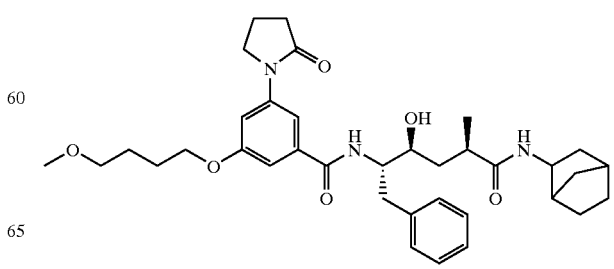

Prepared in an analogous manner to E6 from 3-(4-methoxybutoxy)-5-(2-oxopyrrolidin-1-yl)benzoic acid (D59) and (2R,4S,5S)-5-amino-4-hydroxy-2-methyl-6-phenylhexanoic acid (bicyclo[2.2.1]hept-2-yl)amide (D29).

MS (ES), M+H=620

Abbreviations

DBU 1,8-diazabicyclo[5.4.0]undec-7-ene
DMF dimethylformamide
DMSO dimethylsulfoxide
DME dimethyl ether
THF tetrahydrofuran
DEAD diethylacetylene dicarboxylate
EDC 1-ethyl-3-(3-dimethylaminopropyl)-carbodi-imide hydrochloride
HOBT N-hydroxybenzotriazole
HATU 1,3,3, tetra-methyluronium hexafluorophosphate
DCM dichloromethane
FAM carboxyfluorescein
TAMRA carboxytetramethylrhodamine
[ ] single amino acid letter code relating to peptide sequence Compounds of the invention may be tested for in vitro biological activity in accordance with the following assays:

(I) Asp-2 Inhibitory Assay

For each compound being assayed, in a 384 well plate, is added:

a) 1 μl of a DMSO solution of the test compound ($IC_{50}$ curve uses ten 1 in 2 serial dilutions from 500 μM).

b) 10 μl of substrate (FAM-[SEVNLDAEFK]-TAMRA) solution in buffer. This is prepared by diluting 2 ml of a 2 mM DMSO solution of the substrate into 400 ml of buffer (100 mM Sodium acetate pH=4.5, 1 l Milli-Q water, 0.06% Triton X-100 (0.5 ml/l), pH adjusted to 4.5 using glacial acetic acid). Aminomethyl fluorescein (FAM) and tetramethyl rhodamine (TAMRA) are fluorescent molecules which co-operate to emit fluorescence at 535 nm upon cleavage of the SEVNLDAEFK peptide.

c) 10 μl enzyme solution. This is prepared by diluting 16 ml of a 500 nM enzyme solution into 384 ml of buffer (prepared as above).

Blank wells (enzyme solution replaced by buffer) are included as controls on each plate. Wells are incubated for 1 h at room temperature and fluorescence read using a Tecan Ultra Fluorimeter/Spectrophotometer (485 nm excitation, 535 nm emission).

(II) Asp-1 Inhibitory Assay

For each compound being assayed, in a 384 well plate, is added:

a) 1 μl of a DMSO solution of the test compound ($IC_{50}$ curve uses ten 1 in 2 serial dilutions from 500 μM).

b) 10 μl of substrate (FAM-[SEVNLDAEFK]-TAMRA) solution in buffer. This is prepared by diluting 2 ml of a 2 mM DMSO solution of the substrate into 400 ml of buffer (100 mM Sodium acetate pH=4.5, 1 l Milli-Q water, 0.06% Triton X-100 (0.5 ml/l), pH adjusted to 4.5 using glacial acetic acid).

c) 10 μl enzyme solution. This is prepared by diluting 4 ml of a 6.3 μM enzyme solution into 496 ml of buffer (100 mM Sodium acetate pH=4.5, 40 mM sodium chloride, 900 ml Milli-Q water, 100 ml glycerol, 0.2% CHAPS (2 g/l), pH adjusted to 4.5 using glacial acetic acid).

Blank wells (enzyme solution replaced by buffer) are included as controls on each plate. Wells are incubated for 2 h at room temperature and fluorescence read using a Tecan Ultra Fluorimeter/Spectrophotometer (485 nm excitation, 535 nm emission).

(II) Cathepsin D Inhibitory Assay

For each compound being assayed, in a 384 well plate, is added:

a) 1 μl of a DMSO solution of the test compound ($IC_{50}$ curve uses ten 1 in 2 serial dilutions from 500 μM).

b) 10 μl of substrate (FAM-SEVNLDAEFK-TAMRA) solution in buffer. This is prepared by diluting 2 ml of a 2 mM DMSO solution of the substrate into 400 ml of buffer (100 mM Sodium acetate pH=4.5, 1 l Milli-Q water, 0.06% Triton X-100 (0.5 ml/l), pH adjusted to 4.5 using glacial acetic acid).

c) 10 μl enzyme solution. This is prepared by diluting 1.6 ml of a 200 unit/ml (in 10 mM HCl) enzyme solution into 398.4 ml of buffer (prepared as above).

Blank wells (enzyme solution replaced by buffer) are included as controls on each plate. Wells are incubated for 1 h at room temperature and fluorescence read using a Tecan Ultra Fluorimeter/Spectrophotometer (485 nm excitation, 535 nm emission).

Pharmacological Data

The compound of E1, E3 and E4 were tested in Assays (I), (II) and (III) and the following data was obtained:

| Example | Asp-2 $IC_{50}$ (nM) | Asp-1 $IC_{50}$ (nM) | Cat. D $IC_{50}$ (nM) |
| --- | --- | --- | --- |
| E1 | 600 | 6000 | 13000 |
| E3 | 60 | 420 | 2900 |
| E4 | 35 | 150 | 1800 |

The compounds of E2 and E5–E21 were tested in Assays (I) and (III) and results for all Examples fell within the following ranges of inhibition: 3–200 nM (Asp-2) and 100–3000 nM (CatD).

The compounds of E22–E35 were tested in Assays (I) and (III) and results for all Examples fell within the following ranges of inhibition: 2–900 nM (Asp-2) and 160–3000 nM (CatD).

More particularly, the compounds of E8, 10, 14, 21, 22, 26 and 32 fell within the following ranges of inhibition: 2–30 nM (Asp-2) and 340–3000 nM (CatD).

The invention claimed is:

1. A compound of formula (I):

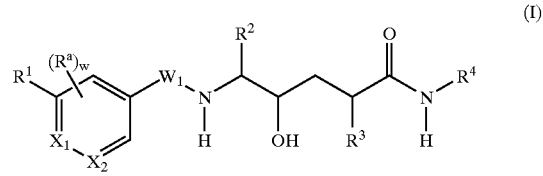

wherein $R^1$ represents a group of formula ($Z^a$) or ($Z^b$):

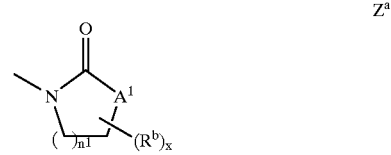

-continued

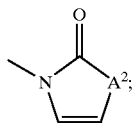

A¹ represents $CH_2$, O, S or $NR^5$;
A² represents O, S or $NR^5$;
$n^1$ represents an integer from 1 to 3;
$R^5$ represents hydrogen, $C_{1-6}$ alkyl optionally substituted by one or more $R^{11}$ groups, $C_{3-8}$ cycloalkyl optionally substituted by one or more $R^{11}$ groups, —$C_{1-2}$ alkyl-$C_{3-8}$ cycloalkyl or aryl;
$R^a$ represents halogen;
$R^b$ represents —$C_{1-6}$ alkyl optionally substituted by one or more $R^{11}$ groups, or —$C_{1-6}$ alkyl-aryl;
$X_1$ represents N, —C(—$R^6$)— or —C(—O—$R^7$)—;
$X_2$ represents N, —C(—$R^8$)— or —C(—Y—$R^9$)—;
Y represents a bond, $CH_2$, O, S, CO, $NR^{10}$, —N($R^{10}$)C(O)—, —C(O)N($R^{10}$)—, COO, aryl, heterocyclyl or heteroaryl;
$R^6$ represents hydrogen, halogen, —$C_{1-6}$ alkyl optionally substituted by one or more $R^{11}$ groups, —$C_{2-6}$ alkenyl, —$C_{3-8}$ cycloalkyl optionally substituted by one or more $R^{11}$ groups, —$C_{1-2}$ alkyl-$C_{3-8}$ cycloalkyl, heteroaryl, heterocyclyl or aryl;
$R^8$ represents halogen or trifluoromethyl;
$R^7$, $R^9$ and $R^{10}$ independently represent hydrogen, —$C_{1-6}$ alkyl optionally substituted by one or more $R^{11}$ groups, —$C_{2-6}$ alkenyl, —$C_{3-8}$ cycloalkyl optionally substituted by one or more $R^{11}$ groups, —$C_{1-2}$ alkyl-$C_{3-8}$ cycloalkyl, heteroaryl, heterocyclyl or aryl;
$W_1$ represents CO or $SO_2$;
$R^2$ represents —$C_{5-8}$ alkyl, —$C_{1-6}$ alkyl-aryl, —$C_{1-6}$ alkyl-heteroaryl, —$C_{1-6}$ alkyl-heterocyclyl, —$C_{1-6}$ alkyl-$C_{3-8}$ cycloalkyl, —$C_{1-6}$ alkyl-S-aryl, —$C_{1-6}$ alkyl-O-aryl, —$C_{1-6}$ alkyl-S-heteroaryl or —$C_{1-6}$ alkyl-O-heteroaryl;
$R^3$ represents —$C_{1-6}$ alkyl optionally substituted by one or more $R^{11}$ groups, or propargyl;
$R^4$ represents —$C_{1-6}$ alkyl optionally substituted by one or more $R^{11}$ groups, —$C_{1-6}$ alkyl-aryl, —$C_{1-6}$ alkyl-heteroaryl, —$C_{1-6}$ alkyl-heterocyclyl, —$C_{1-6}$ alkyl-$C_{3-8}$ cycloalkyl, —$C_{3-8}$ cycloalkyl optionally substituted by one or more groups selected from $R^{11}$ and $C_{1-6}$ alkyl, or propargyl;
w and x independently represent an integer from 0 to 2;
$R^{11}$ represents halogen, hydroxy, —COOH, —COOCH₃, $C_{1-6}$ alkoxy, cyano or amino;
or a pharmaceutically acceptable salt or solvate thereof.

2. A compound of claim 1 wherein $R^1$ represents $Z^a$.
3. A compound of claim 2 wherein A¹ represents $CH_2$.
4. A compound of claim 2 wherein $n^1$ represents 1.
5. A compound of claim 2 wherein x represents 0.
6. A compound claim 1 wherein w represents 0 or 1.
7. A compound claim 6 wherein w represents 1 and $R^a$ represents fluorine.
8. A compound of claim 1 wherein $X_1$ represents —CH.
9. A compound of claim 1 wherein $X_2$ represents —C(Y—$R^9$)—.
10. A compound of claim 9 wherein Y represents a bond, O, —N($R^{10}$)C(O)— or —C(O)N($R^{10}$)—.
11. A compound of claim 9 wherein Y represents a bond, O or —N(H)C(O)—.

12. A compound of claim 9 wherein $R^9$ represents hydrogen, $C_{1-6}$ alkyl optionally substituted with a hydroxy, $C_{1-6}$ alkoxy or $C_{3-8}$ cycloalkyl group, aryl, $C_{2-6}$ alkenyl, $C_{3-8}$ cycloalkyl, $C_{1-6}$ alkoxy or heterocyclyl.
13. A compound of claim 12 wherein $R^9$ represents hydrogen, $C_{1-6}$ alkyl or heterocyclyl.
14. A compound of claim 9 wherein Y represents a bond and $R^9$ represents 2-oxopyrrolidinyl.
15. A compound claim 9 wherein Y represents oxygen and $R^9$ represents $CH(CH_3)_2$.
16. A compound of claim 9 wherein Y represents a bond and $R^9$ represents hydrogen.
17. A compound of claim 9 wherein Y represents NHCO and $R^9$ represents methyl.
18. A compound of claim 1 wherein $W_1$ represents CO.
19. A compound of claim 1 wherein $R^2$ represents unsubstituted benzyl.
20. A compound of claim 1 wherein $R^3$ represents methyl.
21. A compound of claim 1 wherein $R^4$ represents —$C_{3-8}$ cycloalkyl optionally substituted by one or two —$C_{1-6}$ alkyl groups.
22. A compound of claim 21 wherein $R^4$ represents norbornyl, cyclobutyl or cyclohexyl optionally substituted by one or two —$C_{1-6}$ alkyl groups.
23. A compound according to claim 1 which is
N-[(1S,2S,4R)-1-Benzyl-4-(3,3-dimethylbutylcarbamoyl)-2-hydroxypentyl]-4-fluoro-3-(2-oxopyrrolidin-1-yl)-benzamide;
N-[(1S,2S,4R)-1-Benzyl-4-(3,3-dimethylbutylcarbamoyl)-2-hydroxypentyl]-3-hydroxy-5-(2-oxopyrrolidin-1-yl)-benzamide;
3-Allyloxy-N-[(1S,2S,4R)-1-benzyl-4-(3,3-dimethylbutylcarbamoyl)-2-hydroxypentyl]-5-(2-oxopyrrolidin-1-yl)-benzamide;
N-[(1S,2S,4R)-1-Benzyl-4-(3,3-dimethylbutylcarbamoyl)-2-hydroxypentyl]-3-(2-oxopyrrolidin-1-yl)-5-propoxybenzamide;
N-[(1S,2S,4R)-1-Benzyl-4-(3,3-dimethyl-butylcarbamoyl)-2-hydroxypentyl]-3,5-bis-(2-oxo-pyrrolidin-1-yl) benzamide;
N-[(1S,2S,4R)-1-Benzyl-4-(3,3-dimethylbutylcarbamoyl)-2-hydroxypentyl]-3-(2-oxopyrrolidin-1-yl)-5-phenylbenzamide;
N-[(1S,2S,4R)-1-Benzyl-4-(bicyclo[2.2.1]hept-2-ylcarbamoyl)-2-hydroxy-7-methyloctyl]-3,5-bis-(2-oxopyrrolidin-1-yl)benzamide;
N-[(1S,2S,4R)-1-Benzyl-4-(bicyclo[2.2.1]hept-2-ylcarbamoyl)-2-hydroxypentyl]-3,5-bis-(2-oxopyrrolidin-1-yl)benzamide;
N-[(1S,2S,4R)-1-Benzyl-4-(bicyclo[2.2.1]hept-2-ylcarbamoyl)-2-hydroxyhept-6-ynyl]-3,5-bis-(2-oxopyrrolidin-1-yl)benzamide;
3-Acetylamino-N-[(1S,2S,4R)-1-benzyl-4-(bicyclo[2.2.1]hept-2-ylcarbamoyl)-2-hydroxypentyl]-5-(2-oxopyrrolidin-1-yl)benzamide;
N-[(1S,2S,4R)-1-Benzyl-4-(3,3-dimethylbutylcarbamoyl)-2-hydroxypentyl]-3-(2-oxopyrrolidin-1-yl)-5-phenoxybenzamide;
N-[(1S,2S,4R)-1-Benzyl-4-(bicyclo[2.2.1]hept-2-ylcarbamoyl)-2-hydroxypentyl]-3-(3-methoxypropoxy)-5-(2-oxopyrrolidin-1-yl)benzamide;
N-[(1S,2S,4R)-1-Benzyl-4-(bicyclo[2.2.1]hept-2-ylcarbamoyl)-2-hydroxypentyl]-3-(2-hydroxyethoxy)-5-(2-oxopyrrolidin-1-yl)benzamide;

N-[(1S,2S,4R)-1-Benzyl-4-(bicyclo[2.2.1]hept-2-ylcarbamoyl)-2-hydroxypentyl]-3-isopropoxy-5-(2-oxopyrrolidin-1-yl)benzamide;
N-[(1S,2S,4R)-1-Benzyl-4-(bicyclo[2.2.1]hept-2-ylcarbamoyl)-2-hydroxy-pentyl]-3-methoxy-5-(2-oxopiperidin-1-yl)benzamide;
N-[(1S,2S,4R)-1-Benzyl-4-(bicyclo[2.2.1]hept-2-ylcarbamoyl)-2-hydroxypentyl]-3-methoxy-5-(2-oxoazepan-1-yl)benzamide;
N-[(1S,2S,4R)-1-Benzyl-4-(bicyclo[2.2.1]hept-2-ylcarbamoyl)-2-hydroxypentyl]-3-(2-oxooxazolidin-3-yl)benzamide;
N-[(1S,2S,4R)-1-Benzyl-4-(bicyclo[2.2.1]hept-2-ylcarbamoyl)-2-hydroxypentyl]-3-((R)-4-benzyl-2-oxooxazolidin-3-yl)benzamide;
N-[(1S,2S,4R)-1-Benzyl-4-(bicyclo[2.2.1]hept-2-ylcarbamoyl)-2-hydroxy-pentyl]-3-((S)-4-isopropyl-2-oxo-oxazolidin-3-yl)-benzamide;
N-[(1S,2S,4R)-1-Benzyl-4-(bicyclo[2.2.1]hept-2-ylcarbamoyl)-2-hydroxypentyl]-2-fluoro-3-(2-oxopyrrolidin-1-yl)-5-trifluoromethyl-benzamide;
N-[(1S,2S,4R)-1-Benzyl-4-(bicyclo[2.2.1]hept-2-ylcarbamoyl)-2-hydroxypentyl]-2-fluoro-3-(2-oxopyrrolidin-1-yl)-benzamide;
N-[(1S,2S,4R)-1-Benzyl-4-(bicyclo[2.2.1]hept-2-ylcarbamoyl)-2-hydroxypentyl]-2-fluoro-3,5-bis-(2-oxopyrrolidin-1-yl)benzamide;
N-[(1S,2S,4R)-1-Benzyl-4-(bicyclo[2.2.1]hept-2-ylcarbamoyl)-2-hydroxypentyl]-3-cyclopropylmethoxy-5-(2-oxopyrrolidin-1-yl)benzamide;
N-[(1S,2S,4R)-1-Benzyl-4-(bicyclo[2.2.1]hept-2-ylcarbamoyl)-2-hydroxypentyl]-3-cyclobutoxy-5-(2-oxopyrrolidin-1-yl)benzamide;
N-[(1S,2S,4R)-1-Benzyl-4-(bicyclo[2.2.1]hept-2-ylcarbamoyl)-2-hydroxypentyl]-3-((S)-sec-butoxy)-5-(2-oxopyrrolidin-1-yl)benzamide;
N-[(1S,2S,4R)-1-Benzyl-4-(cyclobutylcarbamoyl)-2-hydroxypentyl]-3-isopropoxy-5-(2-oxopyrrolidin-1-yl)benzamide;
N-[(1S,2S,4R)-1-Benzyl-4-(isobutylcarbamoyl)-2-hydroxypentyl]-3-isopropoxy-5-(2-oxopyrrolidin-1-yl)benzamide;
N-[(1S,2S,4R)-1-Benzyl-4-(cyclopropylmethylcarbamoyl)-2-hydroxypentyl]-3-isopropoxy-5-(2-oxopyrrolidin-1-yl)benzamide;
N-[(1S,2S,4R)-1-Benzyl-4-(4,4-dimethylcyclohexylcarbamoyl)-2-hydroxypentyl]-3-isopropoxy-5-(2-oxopyrrolidin-1-yl)benzamide;
N-[(1S,2S,4R)-1-Benzyl-4-(2-cyclohexylethylcarbamoyl)-2-hydroxypentyl]-3-isopropoxy-5-(2-oxopyrrolidin-1-yl)benzamide;
N-[(1S,2S,4R)-1-Benzyl-4-(cyclobutylcarbamoyl)-2-hydroxypentyl]-2-fluoro-3,5-bis-(2-oxopyrrolidin-1-yl)benzamide;
N-[(1S,2S,4R)-1-Benzyl-4-(4-tert-butylcyclohexylcarbamoyl)-2-hydroxypentyl]-2-fluoro-3,5-bis-(2-oxopyrrolidin-1-yl)benzamide;
N-[(1S,2S,4R)-1-Benzyl-4-(bicyclo[2.2.1]hept-2-ylcarbamoyl)-2-hydroxy-pentyl]-N'-methyl-5-(2-oxo-pyrrolidin-1-yl)-N'-propyl-isophthalamide;
N-[(1S,2S,4R)-1-Benzyl-4-(bicyclo[2.2.1]hept-2-ylcarbamoyl)-2-hydroxypentyl]-2-methoxy-6-(2-oxopyrrolidin-1-yl)pyridine-4-carboxamide;
N-[(1S,2S,4R)-1-Benzyl-4-(bicyclo[2.2.1]hept-2-ylcarbamoyl)-2-hydroxypentyl]-3-(4-methoxybutoxy)-5-(2-oxopyrrolidin-1-yl)benzamide;
or a pharmaceutically acceptable salt thereof.

24. A pharmaceutical composition comprising a compound of claim 1 or a pharmaceutically acceptable salt or solvate thereof in admixture with one or more pharmaceutically acceptable diluents or carriers.

25. A method for preparing a compound of claim 1 which comprises at least one process selected from the group consisting of:

(a) reacting a compound of formula (II)

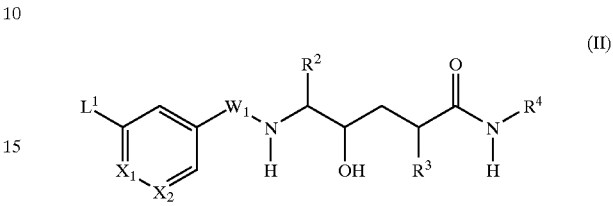

optionally with any hydroxy or amino groups protected, wherein $X_1$, $X_2$, $R^2$, $R^3$, $R^4$ and $W_1$ are as defined in claim 1 and $L^1$ represents a suitable leaving group, with a compound of formula $R^1$—H, wherein $R^1$ is as defined in claim 1, and thereafter optionally as necessary deprotecting a compound of formula (I) which is protected;

(b) reacting a compound of formula (III)

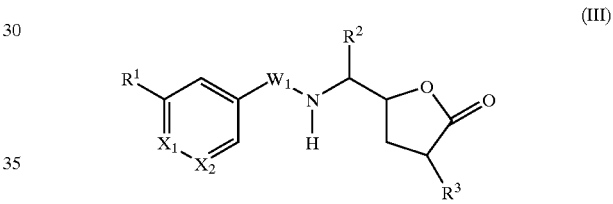

optionally with any hydroxy or amino groups protected, wherein $R^1$, $X_1$, $X_2$, $R^2$, $R^3$ and $W_1$ are as defined in claim 1, with a compound of formula $R^4$—NH$_2$, wherein $R^4$ as defined in claim 1, and thereafter optionally as necessary deprotecting a compound of formula (I) which is protected;

(c) preparing a compound of formula (I) wherein $W_1$ represents CO which comprises reacting a compound of formula (IV)

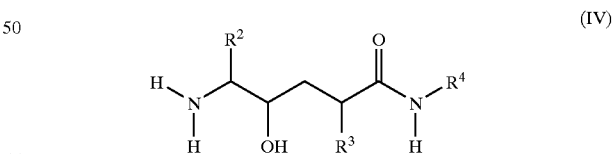

optionally with any hydroxy or amino groups protected, wherein $R^2$, $R^3$ and $R^4$ are as defined in claim 1, with a compound of formula (Va)

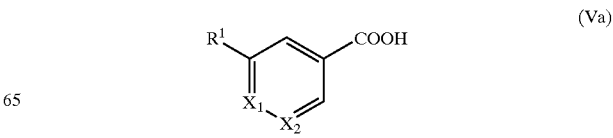

or an activated and optionally protected derivative thereof, wherein $R^1$, $X_1$ and $X_2$ are as defined in claim 1, and thereafter optionally as necessary deprotecting a compound of formula (I) which is protected;

(d) preparing a compound of formula (I) wherein $W_1$ represents $SO_2$ which comprises reacting a compound of formula (IV)

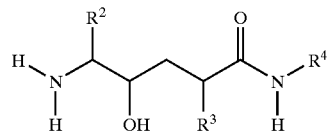
(IV)

optionally with any hydroxy or amino groups protected, wherein $R^2$, $R^3$ and $R^4$ are as defined in claim 1, with a compound of formula (Vb)

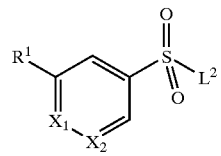
(Vb)

or an optionally protected derivative thereof, wherein $R^1$, $X_1$ and $X_2$ are as defined in claim 1 and $L^2$ represents a suitable leaving group and thereafter optionally as necessary deprotecting a compound of formula (I) which is protected;

(e) deprotecting a compound of formula (I) which is protected; and (f) interconversion of compounds of formula (I) to other compounds of formula (I).

\* \* \* \* \*